US008155730B2

(12) United States Patent
Pertsov et al.

(10) Patent No.: US 8,155,730 B2
(45) Date of Patent: Apr. 10, 2012

(54) COMPOSITION, METHOD, SYSTEM, AND KIT FOR OPTICAL ELECTROPHYSIOLOGY

(75) Inventors: Arkady M. Pertsov, Manlius, NY (US); Arvydas Matiukas, Syracuse, NY (US); Leslie M. Loew, West Hartford, CT (US); Joseph P. Wuskell, West Hartford, CT (US)

(73) Assignee: The Research Foundation of State University of New York, Albany, NY (US)

( * ) Notice: Subject to any disclaimer, the term of this patent is extended or adjusted under 35 U.S.C. 154(b) by 1111 days.

(21) Appl. No.: 11/923,282

(22) Filed: Oct. 24, 2007

(65) Prior Publication Data

US 2008/0097222 A1   Apr. 24, 2008

Related U.S. Application Data

(60) Provisional application No. 60/854,418, filed on Oct. 24, 2006.

(51) Int. Cl.
*A61B 6/00* (2006.01)

(52) U.S. Cl. .......... 600/473; 600/476; 424/9.1; 424/9.6

(58) Field of Classification Search .......... 600/473–480; 424/9.6, 9.1
See application file for complete search history.

(56) References Cited

U.S. PATENT DOCUMENTS

| 5,046,501 | A | * | 9/1991 | Crilly | 600/477 |
|---|---|---|---|---|---|
| 5,127,730 | A | * | 7/1992 | Brelje et al. | 356/318 |
| 5,208,651 | A | * | 5/1993 | Buican | 356/451 |
| 5,304,810 | A | * | 4/1994 | Amos | 250/458.1 |
| 5,419,323 | A | * | 5/1995 | Kittrell et al. | 600/476 |
| 5,494,031 | A | | 2/1996 | Hoeft | |
| 5,562,100 | A | * | 10/1996 | Kittrell et al. | 600/476 |
| 5,583,342 | A | * | 12/1996 | Ichie | 250/459.1 |
| 5,616,502 | A | | 4/1997 | Haugland et al. | |
| 5,627,027 | A | | 5/1997 | Waggoner | |
| 5,631,141 | A | | 5/1997 | Sonek et al. | |
| 5,697,373 | A | * | 12/1997 | Richards-Kortum et al. | 600/475 |
| 5,698,397 | A | * | 12/1997 | Zarling et al. | 435/6.13 |
| 5,842,995 | A | * | 12/1998 | Mahadevan-Jansen et al. | 600/473 |
| 5,862,273 | A | * | 1/1999 | Pelletier | 385/12 |
| 5,865,738 | A | | 2/1999 | Morcos et al. | |
| 5,865,754 | A | * | 2/1999 | Sevick-Muraca et al. | 600/476 |
| 5,955,737 | A | * | 9/1999 | Hallidy et al. | 250/458.1 |
| 6,083,485 | A | | 7/2000 | Licha et al. | |
| 6,151,522 | A | * | 11/2000 | Alfano et al. | 600/473 |
| 6,161,031 | A | * | 12/2000 | Hochman et al. | 600/407 |
| 6,200,310 | B1 | | 3/2001 | Ben-Haim et al. | |
| 6,201,989 | B1 | * | 3/2001 | Whitehead et al. | 600/476 |

(Continued)

OTHER PUBLICATIONS

Matiukas, Arvydas et al., New Near-Infrared Optical Probes of Cardiac Electrical Activity, American Journal of Physiology-Heart and Circulatory Physiology, Jan. 2006, 290, pp. 2633-2643.

(Continued)

*Primary Examiner* — Sanjay Cattungal
(74) *Attorney, Agent, or Firm* — Hoffmann & Baron, LLP

(57) ABSTRACT

The present invention provides a method of optical electrophysiological probing, including: providing a fluorescing chemical probe; contacting a thick portion of tissue with the fluorescing chemical probe to create a thick portion of treated tissue; applying a first range of wavelengths of electromagnetic radiation to the treated portion of tissue; and detecting a plurality of depth-specific emission wavelengths emitted from the thick portion of treated tissue.

11 Claims, 22 Drawing Sheets

U.S. PATENT DOCUMENTS

| | | | |
|---|---|---|---|
| 6,223,069 B1 | 4/2001 | Pfeiffer et al. | |
| 6,258,340 B1 | 7/2001 | Licha et al. | |
| 6,272,376 B1* | 8/2001 | Marcu et al. | 600/477 |
| 6,297,018 B1* | 10/2001 | French et al. | 435/5 |
| 6,339,714 B1 | 1/2002 | Chen | |
| 6,436,095 B1 | 8/2002 | Ben-Haim et al. | |
| 6,441,892 B2* | 8/2002 | Xiao | 356/73 |
| 6,478,424 B1 | 11/2002 | Grinvald et al. | |
| 6,663,847 B1 | 12/2003 | Achilefu et al. | |
| 6,671,540 B1 | 12/2003 | Hochman | |
| 6,757,554 B2 | 6/2004 | Rubinstein et al. | |
| 6,853,857 B2 | 2/2005 | Pfeiffer et al. | |
| 6,869,593 B2 | 3/2005 | Frangioni | |
| 6,887,854 B2 | 5/2005 | Achilefu et al. | |
| 6,913,743 B2 | 7/2005 | Licha et al. | |
| 6,926,885 B2 | 8/2005 | Licha et al. | |
| 7,025,949 B2 | 4/2006 | Licha et al. | |
| 7,087,416 B2 | 8/2006 | Tsien et al. | |
| 7,139,598 B2* | 11/2006 | Hull et al. | 600/317 |
| 7,190,993 B2 | 3/2007 | Sharma et al. | |
| 7,272,252 B2* | 9/2007 | De La Torre-Bueno et al. | 382/133 |
| 7,609,391 B2* | 10/2009 | Betzig | 356/521 |
| 7,889,348 B2* | 2/2011 | Tearney et al. | 356/451 |
| 2002/0158211 A1* | 10/2002 | Gillispie | 250/458.1 |
| 2003/0082105 A1* | 5/2003 | Fischman et al. | 424/9.6 |
| 2003/0108911 A1* | 6/2003 | Klimant et al. | 435/6 |
| 2004/0072200 A1* | 4/2004 | Rigler et al. | 435/6 |
| 2005/0165303 A1* | 7/2005 | Kleen et al. | 600/424 |
| 2006/0147379 A1 | 7/2006 | Bornhop et al. | |
| 2006/0165598 A1 | 7/2006 | Licha et al. | |
| 2006/0165599 A1 | 7/2006 | Licha et al. | |
| 2006/0280687 A1 | 12/2006 | Cheng et al. | |
| 2006/0280688 A1 | 12/2006 | Kovar et al. | |
| 2007/0042398 A1 | 2/2007 | Peng et al. | |
| 2007/0104649 A1 | 5/2007 | Fischer et al. | |
| 2007/0135803 A1 | 6/2007 | Belson | |
| 2007/0223006 A1* | 9/2007 | Tearney et al. | 356/498 |
| 2008/0038686 A1* | 2/2008 | Nagai | 433/29 |
| 2010/0086251 A1* | 4/2010 | Xu et al. | 385/1 |

OTHER PUBLICATIONS

Nygren, A. et al., Voltage-Sensitive Dye Mapping of Activation and Conduction in Adult Mouse Hearts, Annals of Biomedical Engineering, Aug. 2000, 28:8, pp. 958-967, Springer Netherlands.

Matiukas, A., B.G. Mitrea, M. Qin, A.M. Pertsov, A.G. Shvedko, M.D. Warren, A.V. Zaitsev, J.P. Wuskell, M.-d. Wei, J. Watras, and L.M. Loew. 2007. Near Infrared Voltage Sensitive Fluorescent Dyes Optimized for Optical Mapping in Blood-Perfused Myocardium. Heart rhythm : the official journal of the Heart Rhythm Society, 4(11) 1441-51.

Teisseyre, T.Z., A.C. Millard, P. Yan, J.P. Wuskell, M.-d. Wei, A. Lewis, and L.M. Loew. 2007. Non-linear Optical Potentiometric Dyes Optimized for Imaging with 1064 nm Light. J. Biomed. Opt. 12:044001. (Published Aug. 2007).

Wuskell, J.P., D. Boudreau, M.D. Wei, L. Jin, R. Engl, R. Chebolu, A. Bullen, K.D. Hoffacker, J. Kerimo, L.B. Cohen, M. R. Zochowski, and L.M. Loew. 2006. Synthesis, spectra, delivery and potentiometric responses of new styryl dyes with extended spectral ranges. J Neurosci Methods. 151:200-15.

Zhou, W.-L., Y. Ping, J.P. Wuskell, L.M. Loew, and S.D. Antic. 2007. Intracellular long wavelength voltage-sensitive dyes for studying the dynamics of action potentials in axons and thin dendrites. J. Neurosci. Methods. 164:225-239.

\* cited by examiner

JPW 5034

JPW 3067

JPW 5020

Generic A

JPW 6003

JPW 6033 di-4-ANEPPS

Fig. 21A
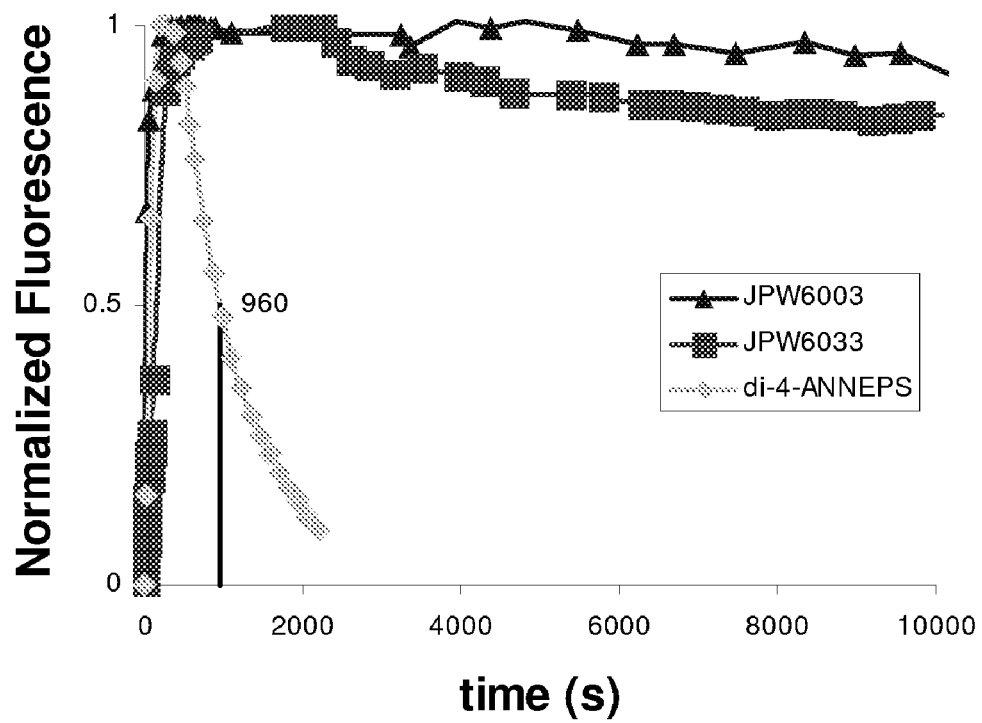
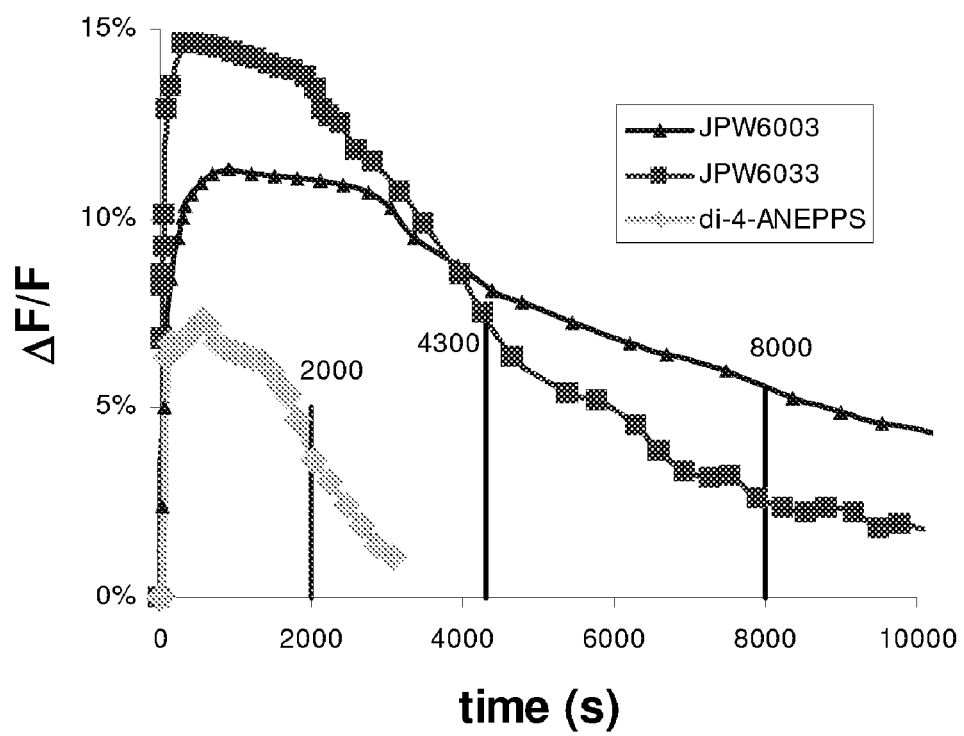
Fig. 21B

*Fig. 22A*
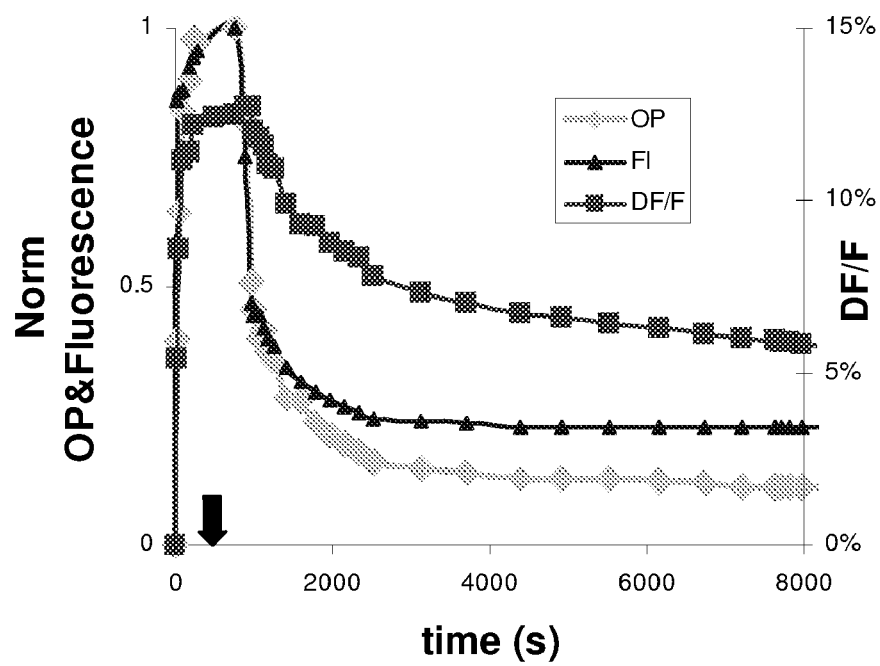
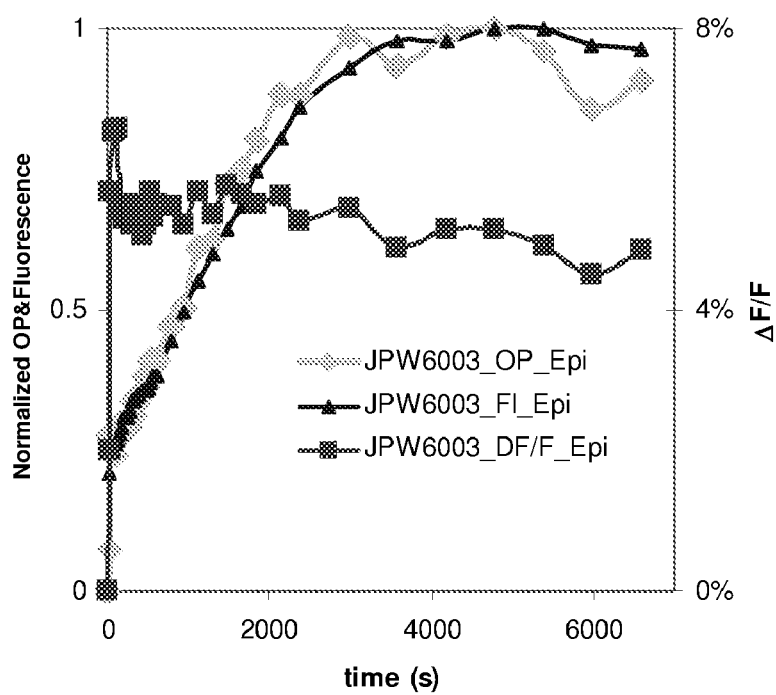
*Fig. 22B*

COMPOSITION, METHOD, SYSTEM, AND KIT FOR OPTICAL ELECTROPHYSIOLOGY

RELATED APPLICATION

The present invention is a non-provisional application which corresponds to U.S. Provisional Application No. 60/854,418 filed Oct. 24, 2006 and entitled "NEAR-INFRARED STYRYL DYES AND METHODS OF USE IN OPTICAL ELECTROPHYSIOLOGY". The aforementioned application is incorporated herein by reference in its entirety.

FUNDING STATEMENT

This invention was made with government support under contract identifier EB-001963 awarded by the National Institute of Health and contract identifier HL-071635 and HL-7163501 awarded by the National Heart Lung and Blood Institute. The government has certain rights in the invention.

BACKGROUND OF THE INVENTION

1. Technical Field

The present invention relates various embodiments of a composition, method, system, and kit for optical electrophysiology. More specifically, the present invention relates to enhanced mapping (and/or optical imaging) of thick tissue with novel near infrared probes (voltage-sensitive dyes) having high voltage sensitivity, including said composition, method, system, and kit for advanced optical methods detailing the electrical activity of an organelle, a cell, a plurality of cells, a tissue, or an organ, including cardiac tissue and neurological tissue.

2. Related Art

A common method for optically imaging the heart tissue of a subject's body is by using microelectrode or patch clamping techniques with branch electrodes. To utilize branch electrodes, multiple leads are used to insert needles into various portions of the heart muscle wall. Once the needles are in place, they record from isolated points inside the muscle. However, branch leads have limitations and drawbacks to their use. Branch leads damage portions of the heart muscle, penetrate the tissue (thereby disrupting cross-sectional continuity), and provide uneven measurements due to the size and displacement of the needles from one another.

These disadvantages have led, in part, to the development of styryl dye, di-4-ANEPPS, which is a voltage-sensitive dye. This dye has been used for optically imaging tissue, including cardiac tissue. However, the di-4-ANEPPS dye has limitations in its use as a voltage probe for cardiac electrophysiology in cells and tissues. Di-4-ANEPPS cannot penetrate thick tissue at depth; di-4-ANEPPS will only afford measurements of optical potentials from only a few hundred micrometers of subsurface layer of tissue. Also, as the excitation wavelength of di-4-ANEPPS is the same range in which blood and tissue typically absorb, at 450 to 550 nanometer range in the electromagnetic spectrum, measurements taken with di-4-ANEPPS typically have high scattering and noise with a low optical resolution, resulting in low image quality even with very high light intensity. Hence, a need exists for voltage-sensitive probes that excite and emit electromagnetic radiation in an electromagnetic range removed from biological interference (i.e. decreased scattering and noise) and provide in depth imaging of thick tissue and/or blood-perfused tissue.

SUMMARY OF THE INVENTION

A first aspect of the present invention provides a method of optical electrophysiological probing, comprising: providing a fluorescing chemical probe, said fluorescing chemical probe having at least one excitation wavelength such that when an electromagnetic radiation of the excitation wavelength is administered to the fluorescing chemical probe, said probe emits electromagnetic radiation of at least one emission wavelength, wherein said excitation wavelength and said emission wavelength are at least about 90 nanometers apart; contacting a thick portion of tissue with said fluorescing chemical probe to create a thick portion of treated tissue; applying a first range of wavelengths of electromagnetic radiation to said treated portion of tissue, said first range of wavelengths of electromagnetic including said excitation wavelength of said fluorescing chemical probe; and detecting a plurality of depth-specific emission wavelengths emitted from said thick portion of treated tissue, said plurality of depth-specific emission wavelengths incremented from a surface of said thick portion of treated tissue to an inner tissue depth from at least about 2.5 millimeters.

A second aspect of the present invention provides an optically mapping composition comprising a voltage-sensitive dye of the formula:

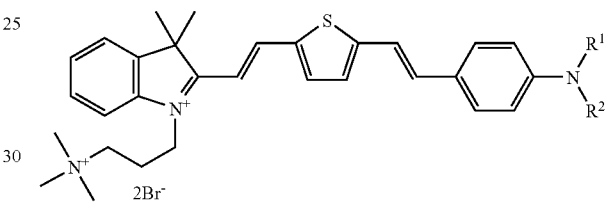

wherein R1 includes a first hydrocarbon chain and R2 includes a second hydrocarbon chain of a length of carbon chains.

A third aspect of the present invention provides a system of in-depth in vivo imaging, comprising: a dosage of a fluorescing chemical probe, characteristic in that said probe has an excitation wavelength and an emission wavelength, said excitation wavelength differs by at least about 90 nanometers or more from said emission wavelength, said probe configured to be biologically compatible to a subject tissue; an illumination source, said illumination source configured to illuminate a dosed portion of said subject tissue; a photodetector, configured to detect a plurality of emission wavelength readings from a surface of said subject tissue to at least about 2.5 millimeters of tissue depth; and a computer system, configured to collect and record said plurality of emission wavelength readings.

A fourth aspect of the present invention provides: An optical probing kit for tissue, comprising: a fluorescing probe quantity, said fluorescing probe quantity configured to emit an electromagnetic radiation emission at about 600 to about 1000 nanometers; an instruction for administering said fluorescing probe quantity; and a delivery member; said delivery member configured to deliver said fluorescing probe quantity into a portion of tissue.

BRIEF DESCRIPTION OF THE DRAWINGS

The present invention is described in detail below with reference to the drawings in which:

FIG. 21A depicts an illustration of experimental data acquired with respect to the various fluorescing chemical probes with respect to the present invention; and FIG. 21B depicts an illustration of experimental data acquired with respect to the various fluorescing chemical probes with respect to the present invention; and FIG. 22A depicts an illustration of experimental data acquired with respect to the various fluorescing chemical probes with respect to the present invention; and FIG. 22B depicts an illustration of experimental data acquired with respect to the various fluorescing chemical probes with respect to the present invention.

DETAILED DESCRIPTION OF THE INVENTION

Figure 1:
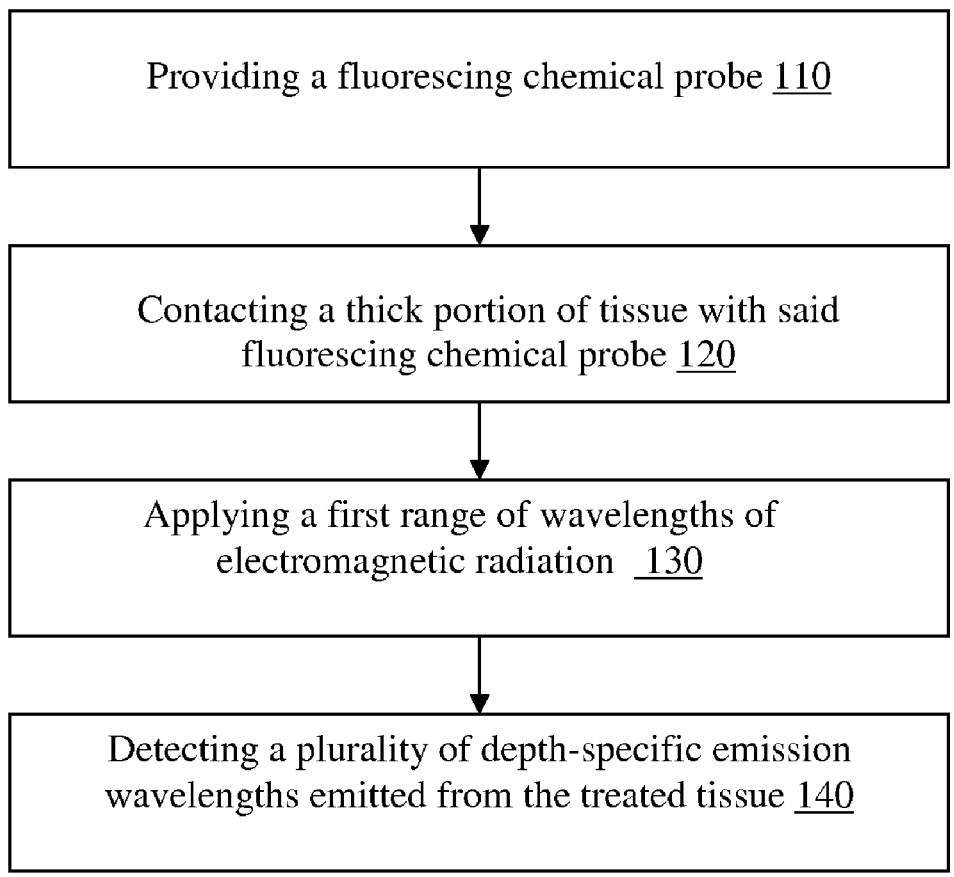
FIG. 1 depicts a flowchart of an example of an embodiment of the method of the present invention.
Figure 2:
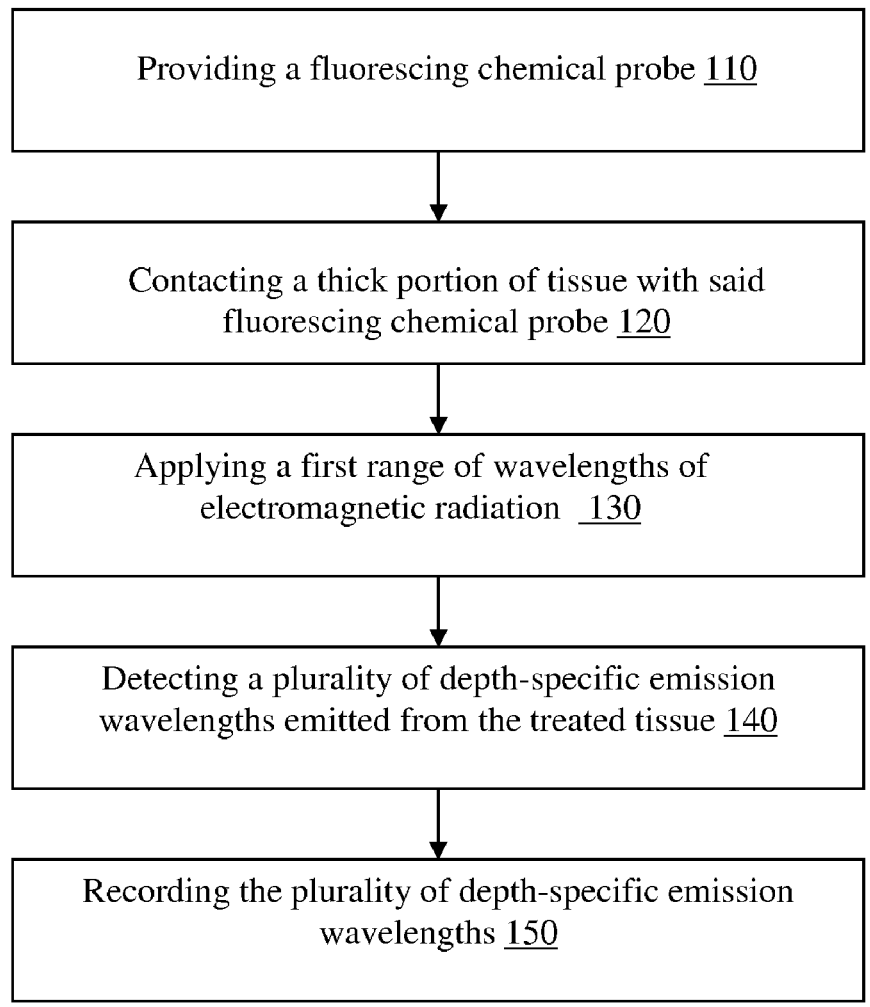
FIG. 2 depicts a flowchart of another example of an embodiment of the method of the present invention.
Figure 3:
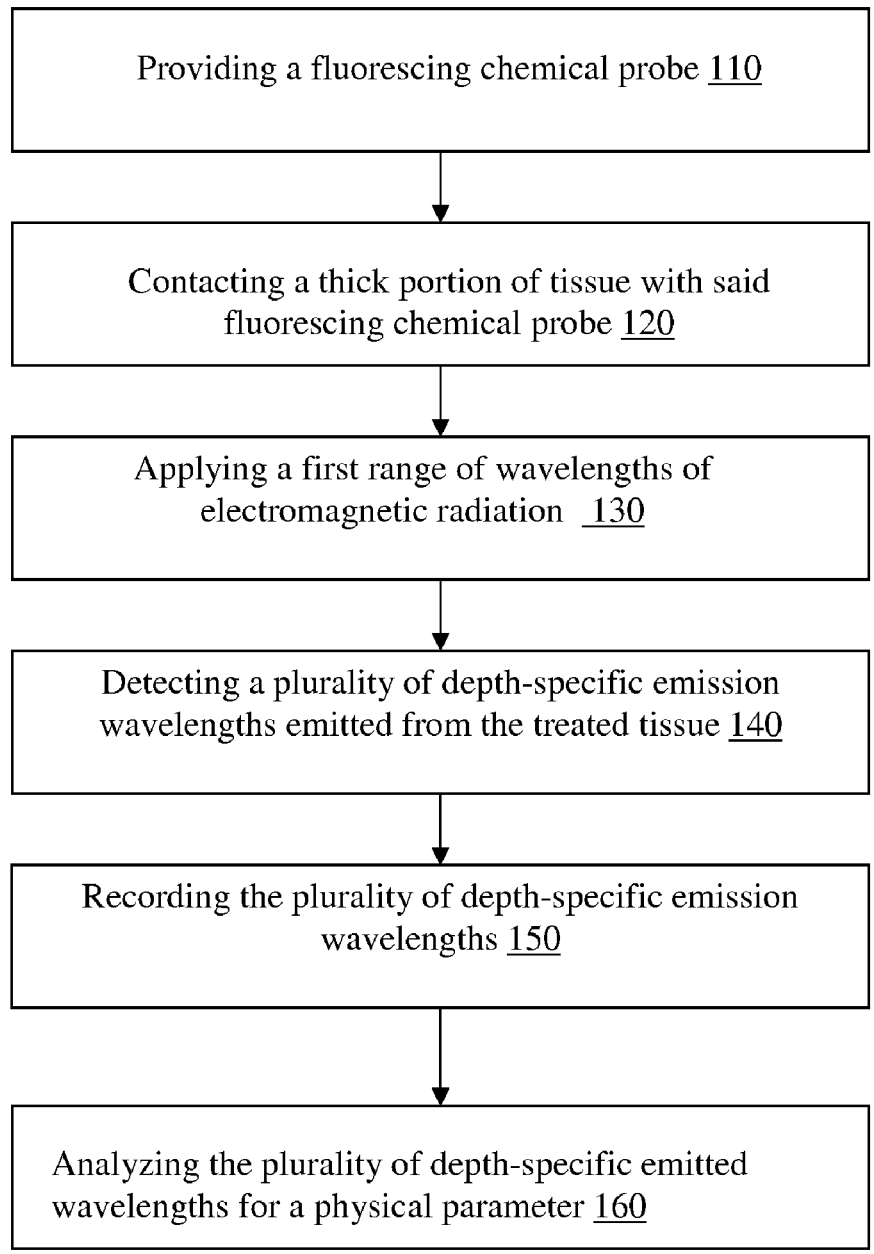
FIG. 3 depicts a flowchart of still another example of an embodiment of the method of the present invention.
Figure 4:
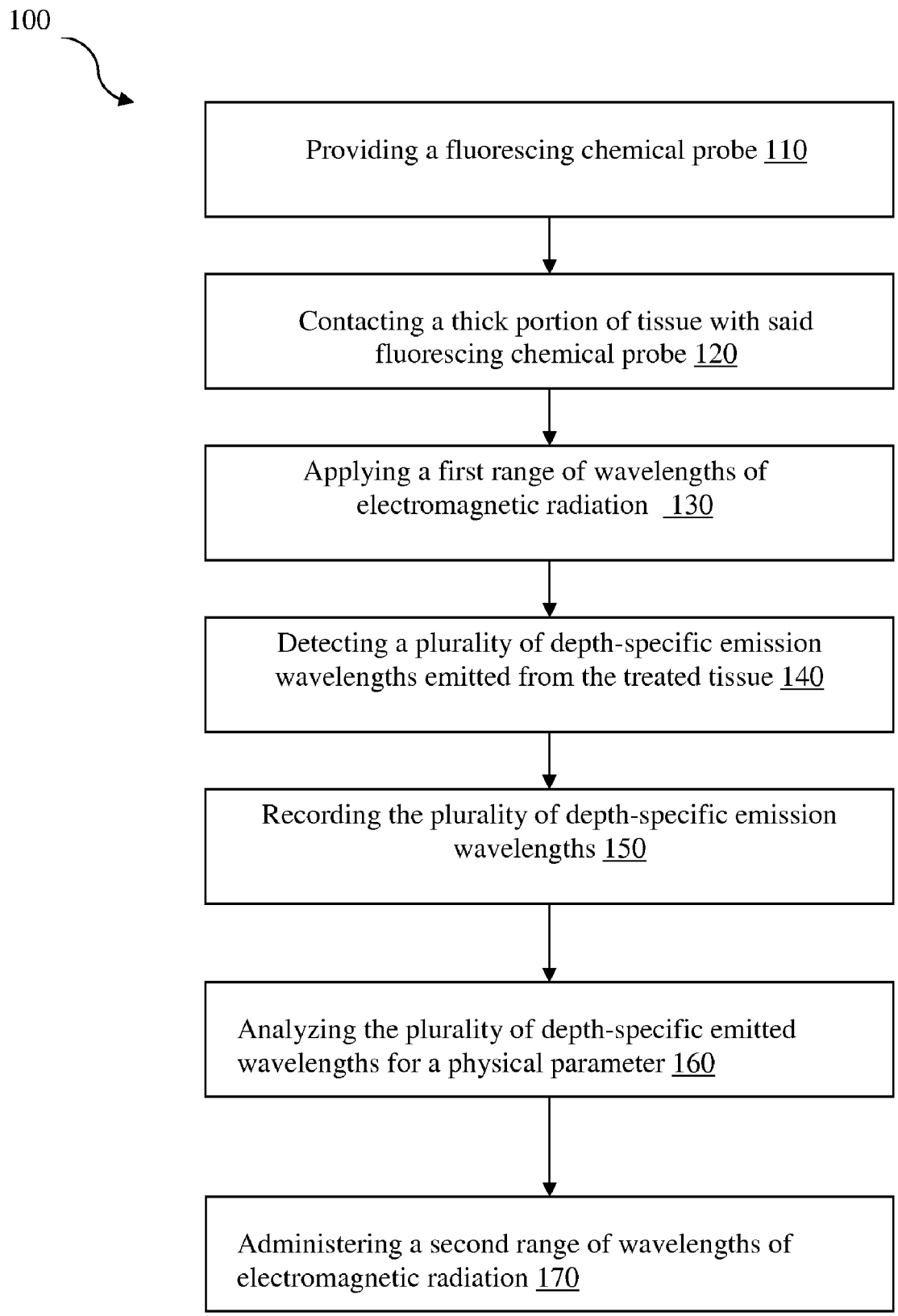
FIG. 4 depicts a flowchart of still yet another example of an embodiment of the method of the present invention.
Figure 5:
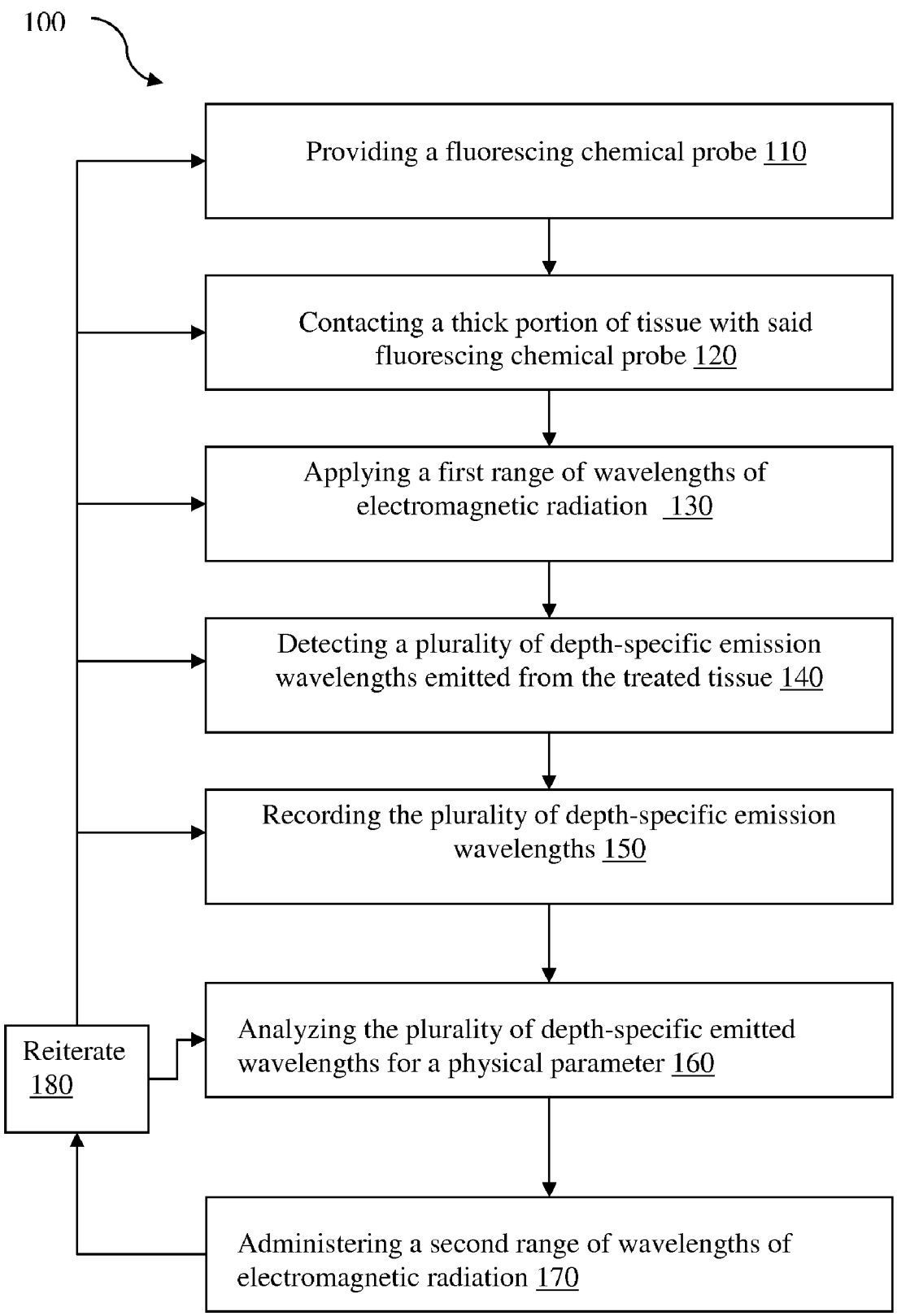
FIG. 5 depicts a flowchart of further an example of an embodiment of the method of the present invention.

The present invention provides a method, composition, system, and kit for optical electrophysiology of in situ tissue, and may further include cardiology and neurology applications. Voltage sensitive dyes, also referred to as voltage sensitive probes herein, may be used to facilitate diagnostic tests, modeling programs, imaging procedures, as well as optical probing kits. Further to the present invention, the following paragraphs provide additional discussion and disclosure of the various embodiments of the present invention, as well as various examples of those embodiments. Although the various embodiments of the method, composition of matter, system, and kit of the present invention will be discussed and disclosed in detail inter alia, it should be understood by those skilled in the art that the applications referenced here and the various examples and embodiments of the present invention may be used in the heart, in the brain, or throughout the body of an organism, including warm blooded animals, for mapping of the electrical potential of a single cell, various portions of tissue, and/or organs.

It would be advantageous for the voltage-sensitive probes to have fast response time, high voltage sensitivity, a wide range of dye-loading constants, low washout time constants, and/or a low photo bleaching effect in vivo. Further, it would be advantageous for the voltage-sensitive probes which may be used to measure the membrane potentials across the inner membranes of individual mitochondria within a single living cell, investigate spiral and scroll waves in millimeter-thick layers or across whole ventricular wall (at or above 10 mm thickness), reconstruct three-dimensional scroll waves in a modeling program, probe deep tissues, map blood-perfused tissue, and provide more efficient double-dye ($Ca/V_m$) optical mapping. Also, the voltage-sensitive probe may have one or more advantageous properties for performing these tasks at high efficiency and effectiveness, including efficient loading, low toxicity, and voltage-sensitive efficiency.

Incorporated by reference by their entirety are the following publications, including: Matiukas, A., B. G. Mitrea, A. M. Pertsov, J. P. Wuskell, M. D. Wei, J. Watras, A. C. Millard, and L. M. Loew. 2006. New near-infrared optical probes of cardiac electrical activity. *Am J Physiol Heart Circ Physiol.* 290:H2633-43.; Matiukas, A., B. G. Mitrea, M. Qin, A. M. Pertsov, A. G. Shvedko, M. D. Warren, A. V. Zaitsev, J. P. Wuskell, M.-d. Wei, J. Watras, and L. M. Loew. 2007. Near Infrared Voltage Sensitive Fluorescent Dyes Optimized for Optical Mapping in Blood-Perfused Myocardium. *Heart rhythm: the official journal of the Heart Rhythm Society.*; Wuskell, J. P., D. Boudreau, M. D. Wei, L. Jin, R. Engl, R. Chebolu, A. Bullen, K. D. Hoffacker, J. Kerimo, L. B. Cohen, M. R. Zochowski, and L. M. Loew. 2006. Synthesis, spectra, delivery and potentiometric responses of new styryl dyes with extended spectral ranges. *J Neurosci Methods.* 151:200-15.; Teisseyre, T. Z., A. C. Millard, P. Yan, J. P. Wuskell, M.-d. Wei, A. Lewis, and L. M. Loew. 2007. Non-linear Optical Potentiometric Dyes Optimized for Imaging with 1064 nm Light. *J. Biomed. Opt.* 12:044001. (Published August 2007); and Zhou, W.-L., Y. Ping, J. P. Wuskell, L. M. Loew, and S. D. Antic. 2007. Intracellular long wavelength voltage-sensitive dyes for studying the dynamics of action potentials in axons and thin dendrites. *J. Neurosci. Methods.* 164:225-239.

An example of an embodiment of the present invention includes a method of optical electrophysiological probing 100. The method may be shown and described, for example, in FIG. 1 through FIG. 5. The method of optical electrophysiological probing 100 may comprise, for example, providing a fluorescing chemical probe 110; contacting a thick portion of tissue with said fluorescing chemical probe to create a thick portion of treated tissue 120; applying a first range of wavelengths of electromagnetic radiation to said treated portion of tissue 130, said first range of wavelengths of electromagnetic including said excitation wavelength of said fluorescing chemical probe; and detecting a plurality of depth-specific emission wavelengths emitted from said thick portion of treated tissue 140, said plurality of depth-specific emission wavelengths incremented from a surface of said thick portion of treated tissue to an inner tissue depth at least about 2.5 millimeters.

Providing a fluorescing chemical probe 110 may include a fluorescing chemical probe 200. The fluorescing chemical probe 200 may have both at least an excitation wavelength 210 and at least an emission wavelength 220. That is, the fluorescing chemical probe 200 may have more than one excitation wavelength 210 or emission wavelength 220. The respective emission wavelengths and excitation wavelengths may be present in, for example, a band of wavelengths. Also, the excitation wavelength 210 of electromagnetic radiation may be, for example, past the range of wavelengths in which biological tissue absorbs, between about 480 to 550 nm.

When the fluorescing chemical probe 200 may be illuminated with electromagnetic radiation within its range or band of excitation wavelength 210, the fluorescing chemical probe 200 may absorb the electromagnetic radiation such that the radiation places the fluorescing chemical probe 200 in an excited state. While in the excited state, the fluorescing chemical probe 200 may emit electromagnetic radiation at an emission wavelength 220. For example, an excitation wavelength may be an electromagnetic radiation wavelength from at least about 630 nm. An emission wavelength may be an electromagnetic radiation wavelength from at least about 700 to about 900 nm.

The fluorescing chemical probe 200 may be designed such that the excitation wavelength 210 of electromagnetic radiation and the emission wavelength 220 of electromagnetic radiation may be about 90 nanometers apart. In such a manner, ascertaining the difference between electromagnetic radiation administered to the fluorescing chemical probe 200 and the electromagnetic radiation emitted from the excited fluorescing chemical probe 200 molecules may be easily differentiated, filtered, and measured for voltage intensity.

In reference to the fluorescing chemical probe 200, this may refer to a voltage-sensitive dye, for example, a near infrared voltage sensitive dye. Also, fluorescing chemical probe 200 may both excite from and emit radiation in the electromagnetic spectrum that may exceed or have a wavelength greater than 600 nanometers. The operable range, which includes both the excitation and emission ranges of the dyes, may be in the visible red, in the near infrared, and/or in the infrared, ranging, for example, from about 600 nm to about 1000 nm.

The fluorescing chemical probes 200 that may be utilized in the method of optical electrophysiological probing 100 may comprise, for example, novel derivatives of one or more dyes in the styryl class of compounds. The dyes may measure and respond to fast electrophysiological processes that occur in cell membranes. Some examples of these processes include ionic currents (currents of ion channels) that may in effect build action potential of a cell. Another example of a fast electrophysiological process may include an external electric field that may depolarize or polarize the cell membrane of a cell as in the case of electric defibrillation of the heart. For example, the probes 200 may include various dyes from the JPW class of compounds synthesized originally by Joeseph P. Wuskell and Leslie Loew at the University of Connecticut Health Center. Some examples of fluorescing chemical probes 200 are depicted, for example, in FIG. 11 through FIG. 12. The synthesis of these two classes of dye compounds may be shown and described, for example, in FIG. 13 through FIG. 16.

Figure 11:
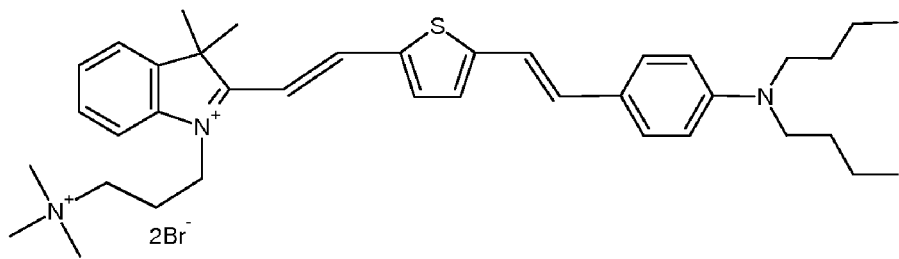
FIG. 11 depicts an illustration of examples of an embodiment of the composition of matter of the present invention.
Figure 11:
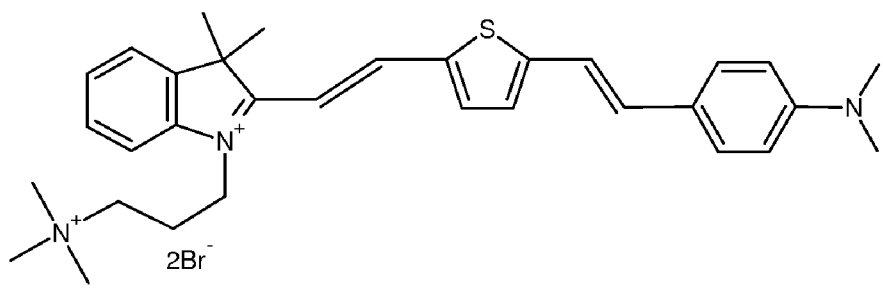
Figure 11:
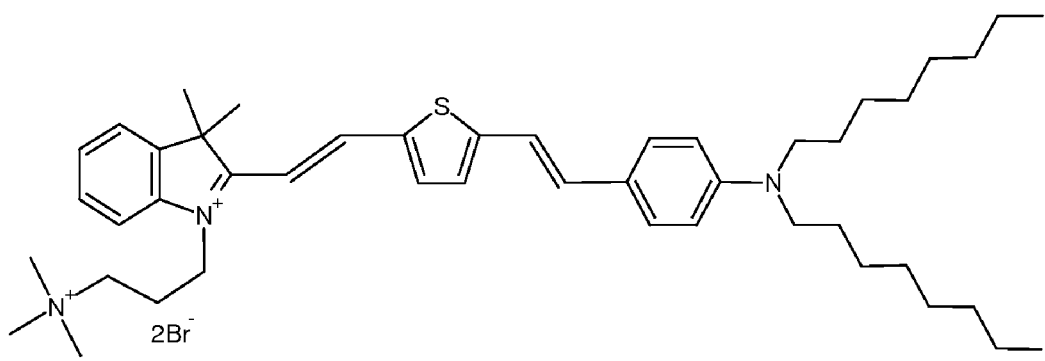
Figure 11:
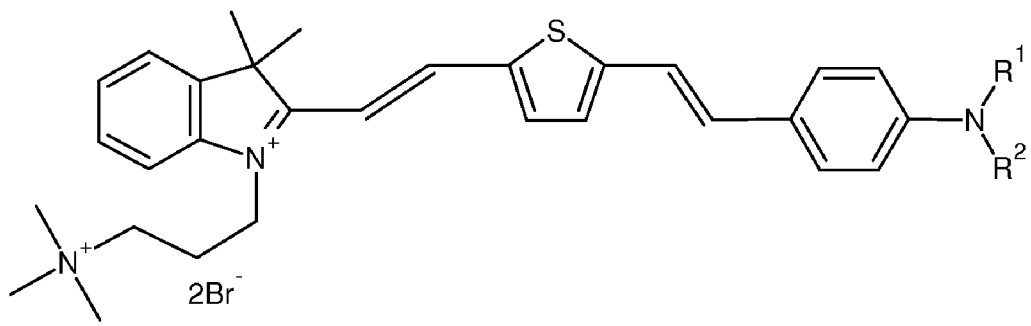

Referring to FIG. 11, the first class of dyes, may be referred to as Class A, including, JPW 3067, JPW 5020, JPW 5034, and generic class A, respectively. All three fluorescing chemical probes JPW 3067, JPW 5020, and JPW 5034 have the same chromophore, but may differ by the length of hydrocarbon chains. Molecular weights of three class A examples, including JPW 3067, JPW 5020, and JPW 5034 are 659.59 g/mol, 743.74 g/mol, and 855.95 g/mol, respectively. The JPW 3067, JPW 5020, and JPW 5034 may each have an absorbance spectra which may reveal several maxima that have variable amplitudes under different pH or solvent conditions and may represent different configurational isomers. The probes may absorb out to around 800 nm. The class A probes comprise absorption and emission peaks that occur at wavelengths 150 nm longer than those of di-4-ANEPPS.

Figure 12:
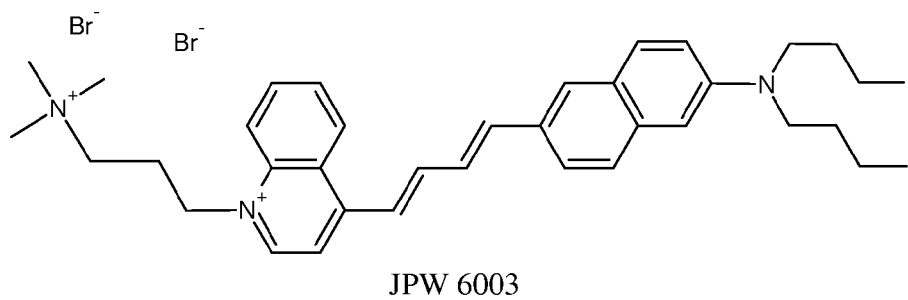
FIG. 12 depicts an illustration of examples of an embodiment of fluorescing chemical probes of the present invention.
Figure 12:
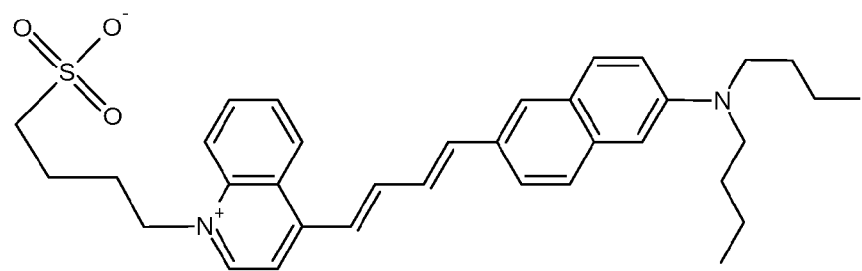
Figure 12:
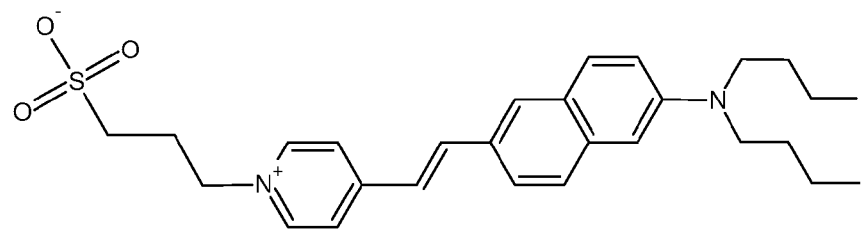
Figure 13:
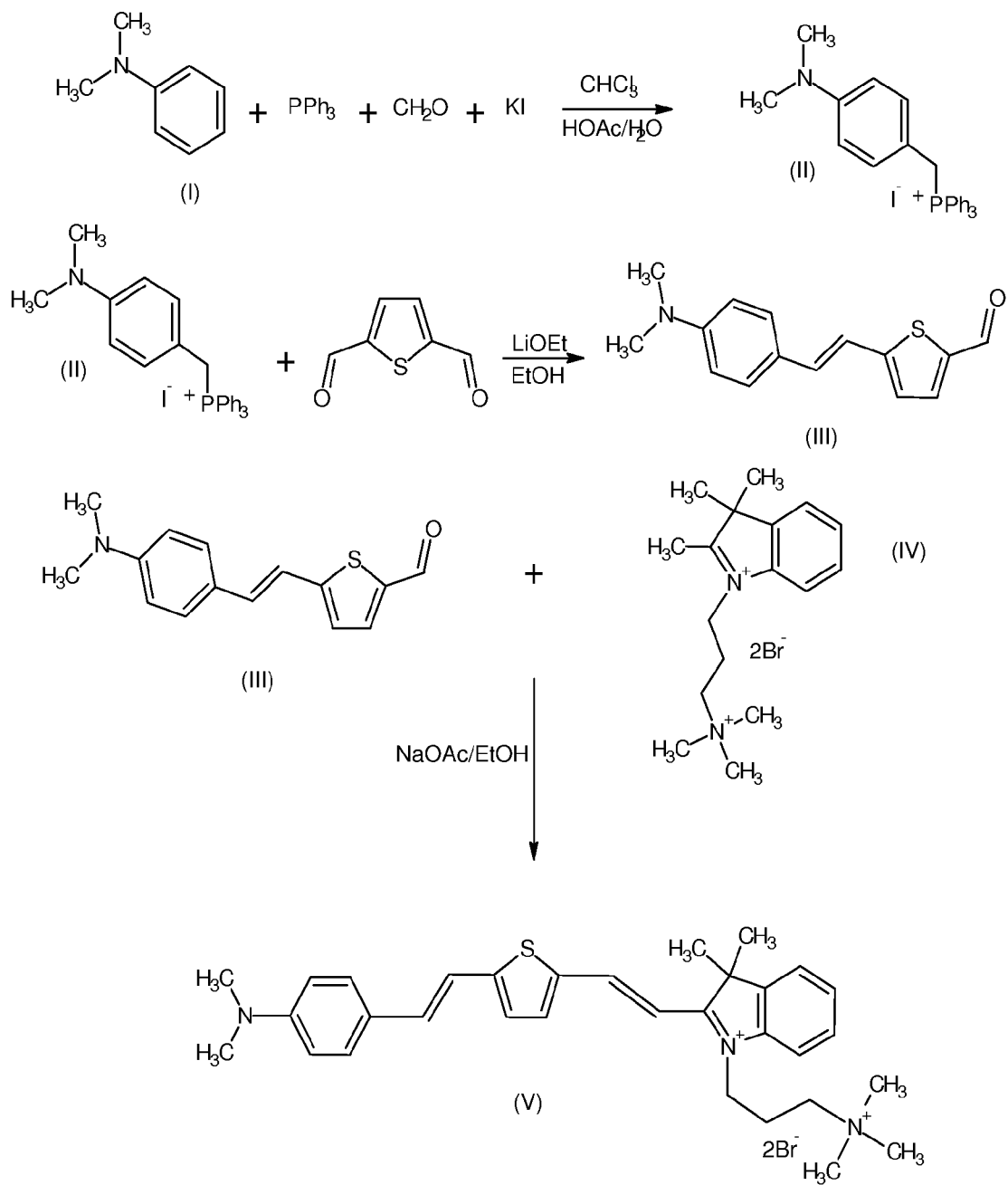
FIG. 13 depicts an illustration of a chemical synthesis for an exemplary embodiment of a composition of matter of the present invention.
Figure 14:
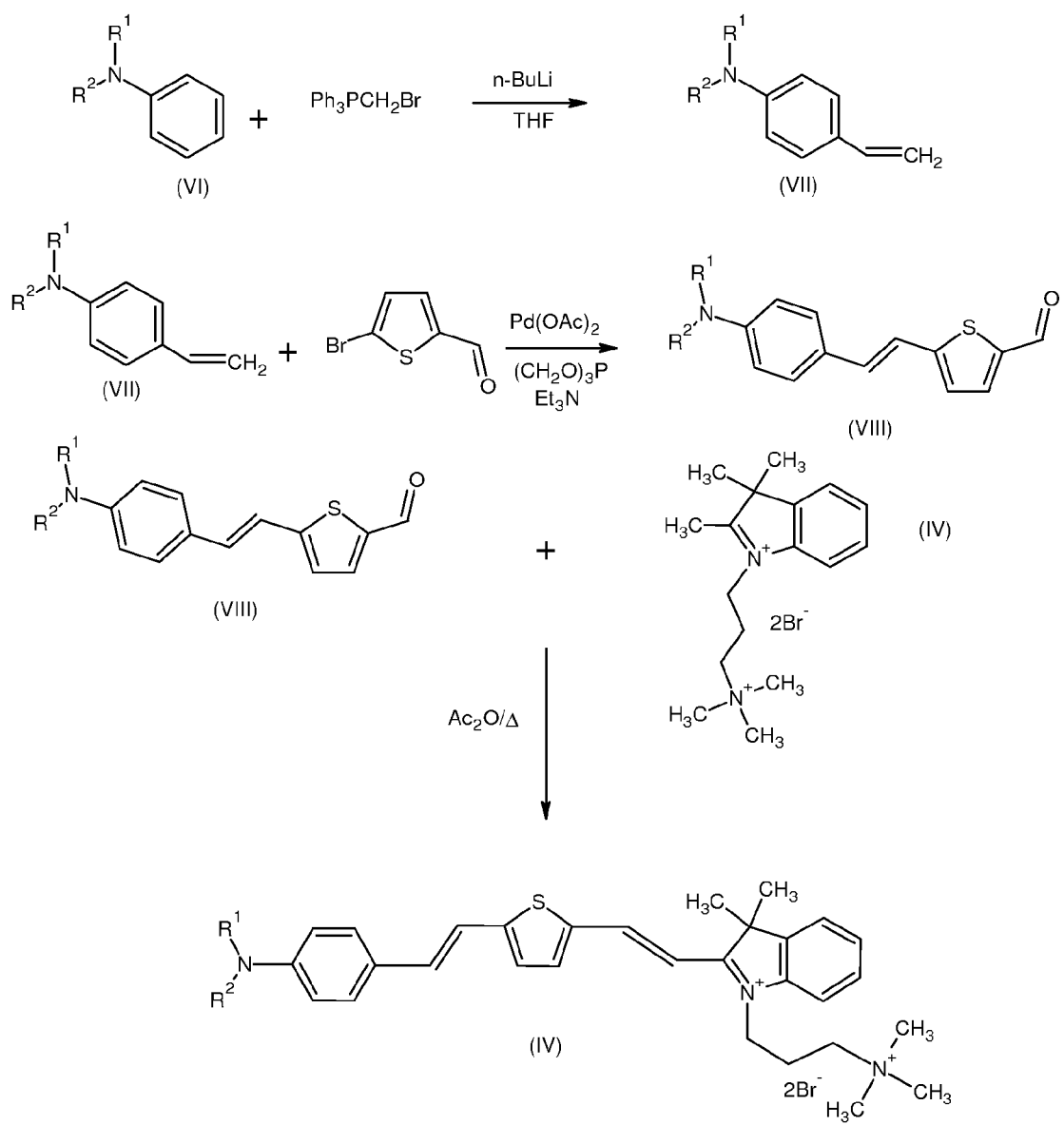
FIG. 14 depicts another illustration of a chemical synthesis for an exemplary embodiment of a composition of matter of the present invention.
Figure 15:
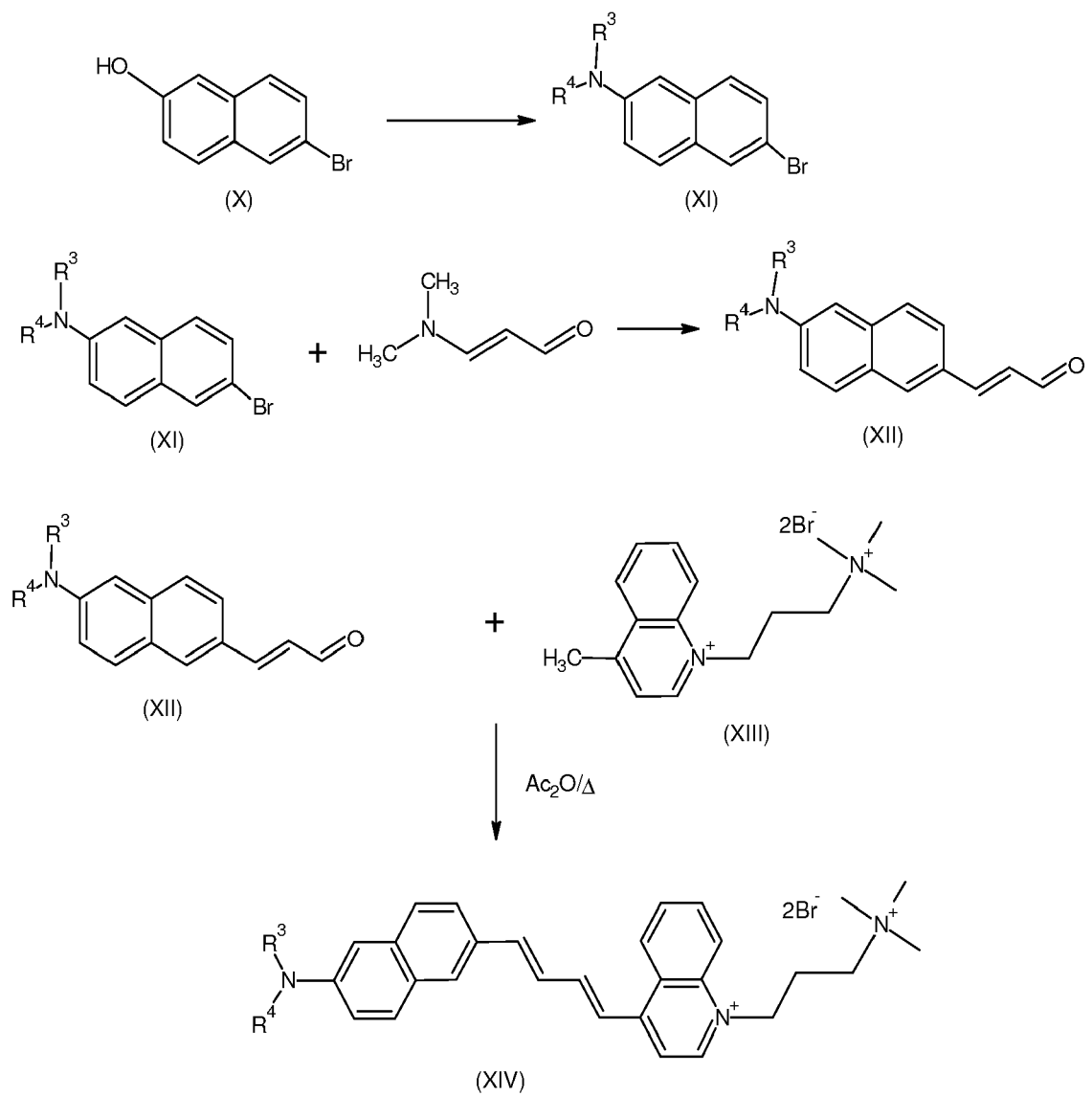
FIG. 15 depicts an illustration of an example of a fluorescing chemical probe of an embodiment of the present invention.
Figure 16:
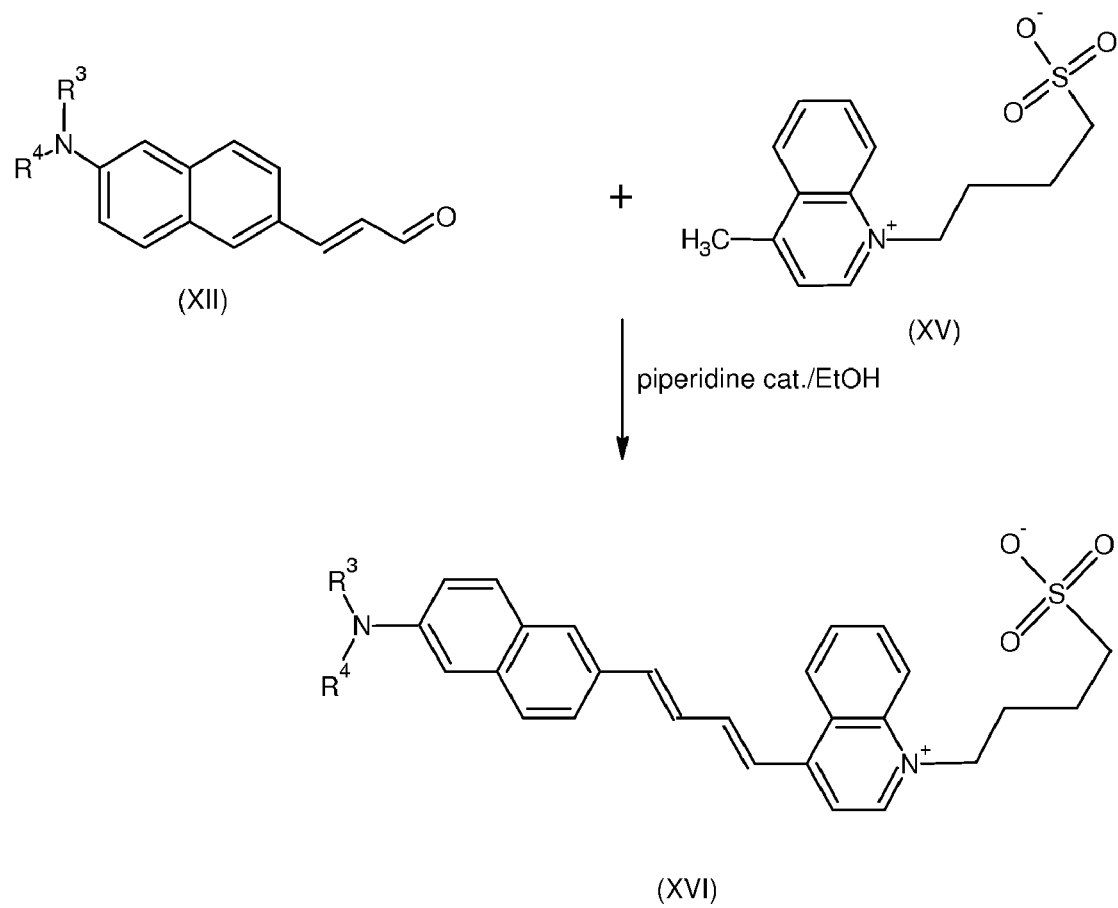
FIG. 16 depicts another illustration of an example of a fluorescing chemical probe of an embodiment of the present invention.

Referring to FIG. 12, the second class of dyes may be referred to as Class B, including JPW 6003 (Di-4-ANB-DQPQ) and JPW 6033 (Di-4-ANBDQBS), with Di-4-ANEPPS for comparison. Both dyes in class B have the same chromophore, but may differ by quaternary ammonium and butylsulfonate polar groups. The molecular weights two class B example dyes, JPW 6003 and JPW 6033, are 695.63 g/mol, and 570.73 g/mol, respectively. The absorption maxima (excitation wavelength) for JPW 6003 in ethanol occurred at 603 nm. For the dye JPW 6033, absorption maxima (excitation wavelength) may shift 20-40 nm to shorter wavelengths, but absorbance is two to three times higher than JPW 6003. Though the long wavelength absorbance peaks of class B fluorescing chemical probes may range from 561 nm to 603 nm in ethanol, and 526 nm to 539 nm in a model membrane made of multilamellar lipid vesicles (MLV), in practical applications, both fluorescing chemical probes 200 may be efficiently excited over a much broader range (500-700 nm), allowing one to optimize excitation for the dye in different tissues, including blood perfused tissue. When class B probes may be excited at 560 nm in ethanol, both probes emit over the range 700-900 nm, though the fluorescence of JPW 6033 in ethanol is much lower. In MLVs, the fluorescence of JPW 6033 to 520 nm light is considerably higher, with emission over the range 600-800 nm, and peak fluorescence slightly greater than that of JPW6003. In myocardium, both class A voltage sensitive dyes and class B voltage sensitive dyes may emit fluoresce in the form of emission wavelength in the near infrared region 700-900 nm.

Figure 17A:
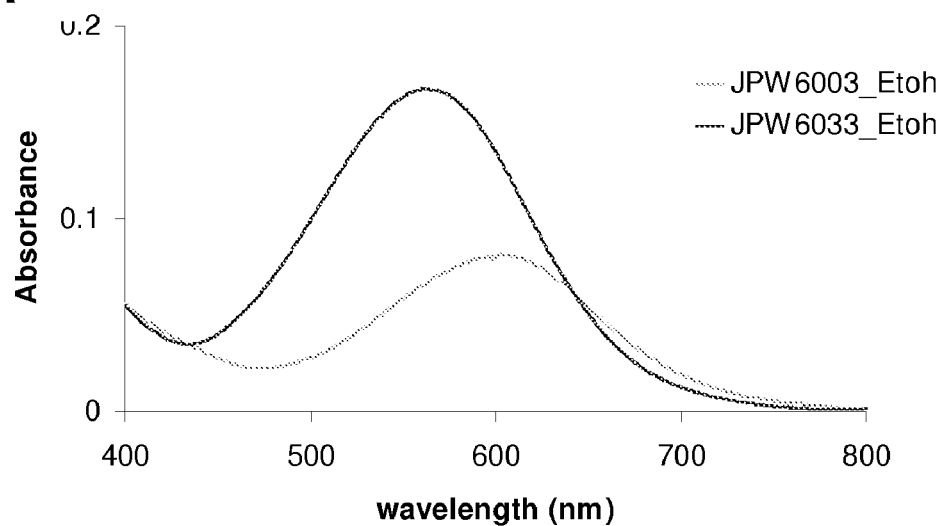
FIG. 17A depicts an illustration of experimental data acquired with respect to the various fluorescing chemical probes with respect to the present invention.
Figure 17B:
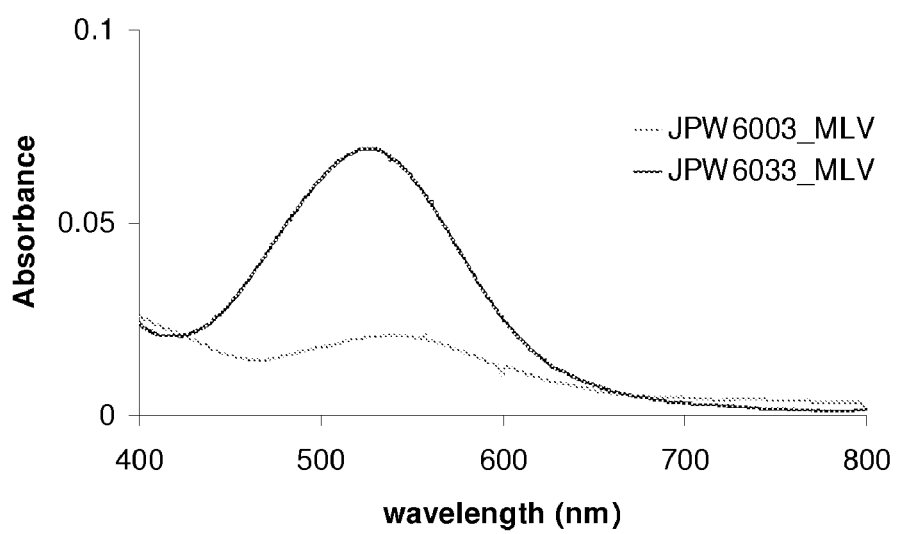
FIG. 17B depicts an illustration of experimental data acquired with respect to the various fluorescing chemical probes with respect to the present invention.
Figure 18A:
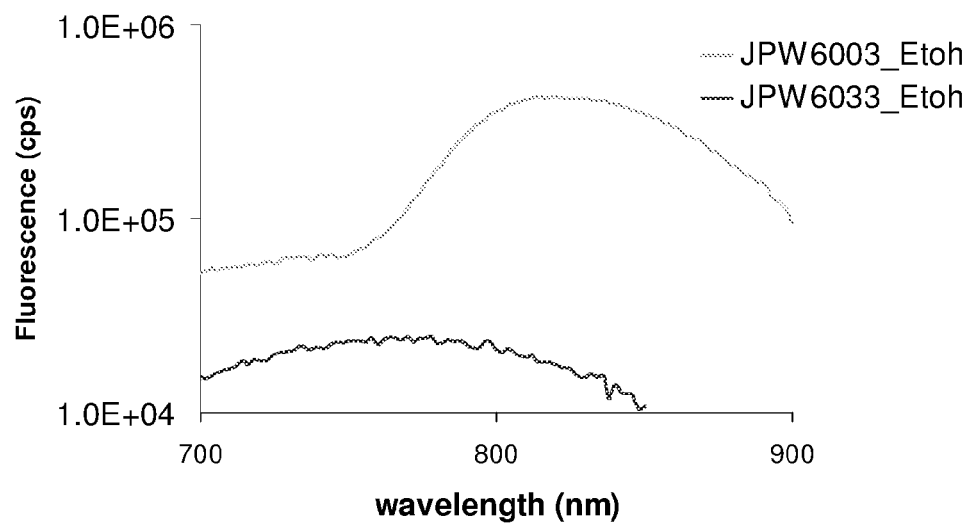
FIG. 18A depicts an illustration of experimental data acquired with respect to the various fluorescing chemical probes with respect to the present invention.
Figure 18B:
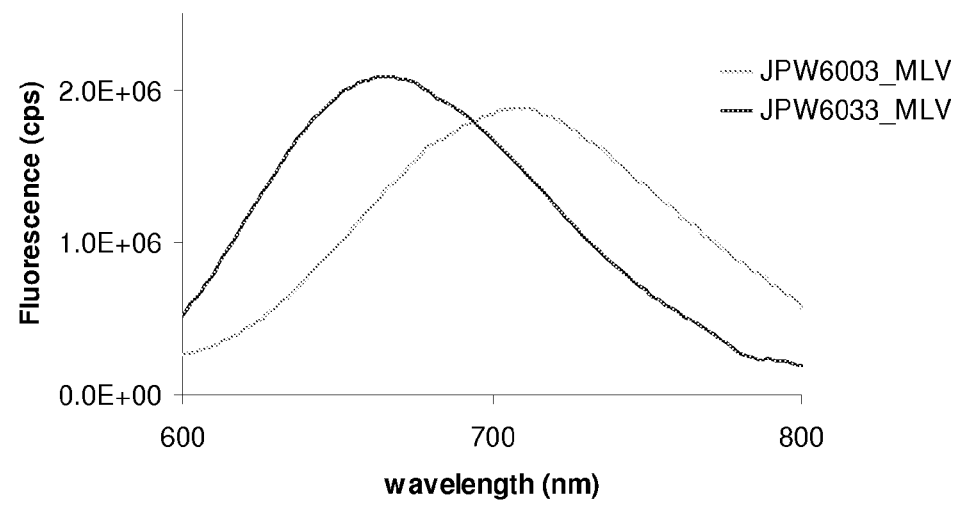
FIG. 18B depicts an illustration of experimental data acquired with respect to the various fluorescing chemical probes with respect to the present invention.
Figure 19A:
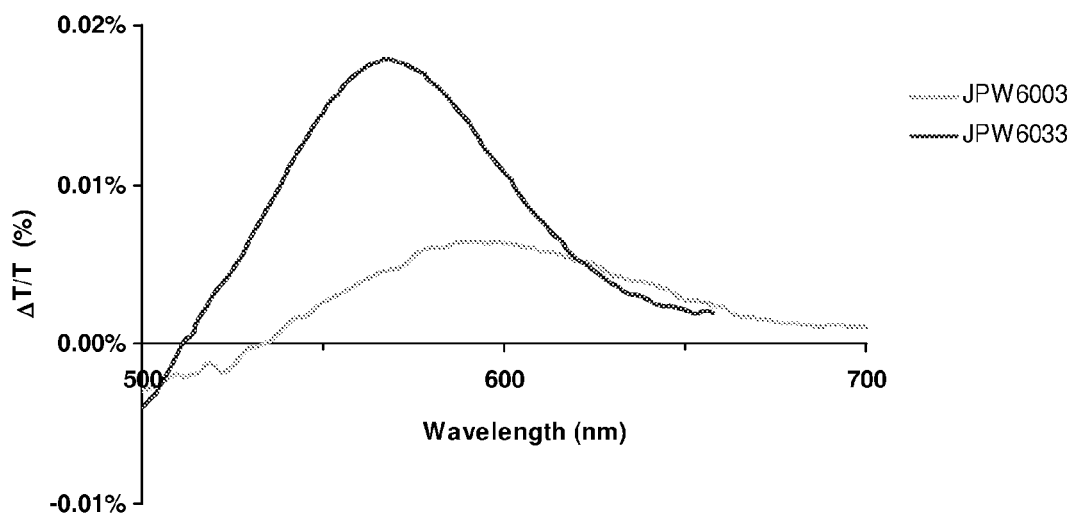
FIG. 19A depicts an illustration of experimental data acquired with respect to the various fluorescing chemical probes with respect to the present invention.
Figure 19B:
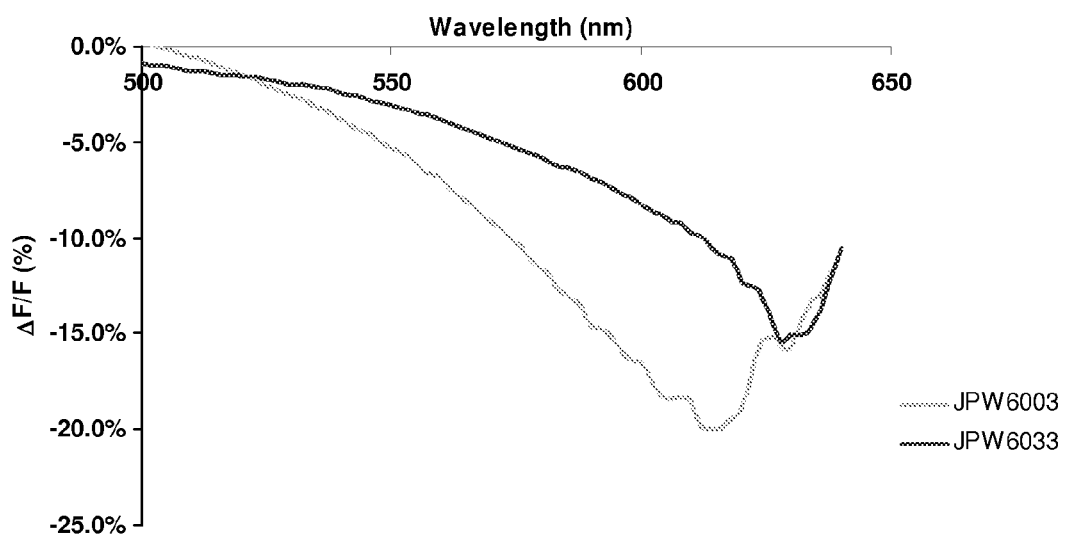
FIG. 19B depicts an illustration of experimental data acquired with respect to the various fluorescing chemical probes with respect to the present invention.

Various figures support one or more characteristics of the fluorescing chemical probes 200 of class B, including, for example, JPW 6003 and JPW 6033. FIG. 17 illustrates the Dye absorbances in ethanol (FIG. 17A) and multilamellar lipid vesicles (FIG. 17B). FIG. 18 depicts dye emission spectra in ethanol (FIG. 18A), and multilamellar lipid vesicles (FIG. 18B). FIG. 19 depicts the wavelength dependent relative transmitted light (FIG. 19A) and fluorescence (FIG. 19B) responses on the hemispherical lipid bilayer (HLB) for 100 mV voltage steps. In FIG. 19B, the fluorescence emission was collected through a >715 nm cutoff filter.

Figure 20A:
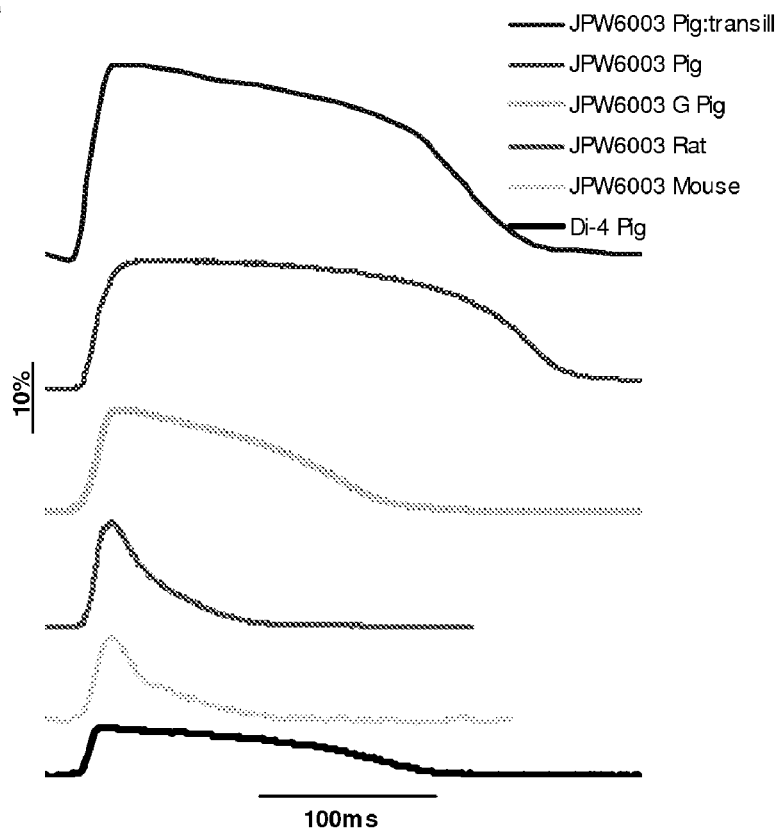
FIG. 20A depicts an illustration of experimental data acquired with respect to the various fluorescing chemical probes with respect to the present invention.
Figure 20B:
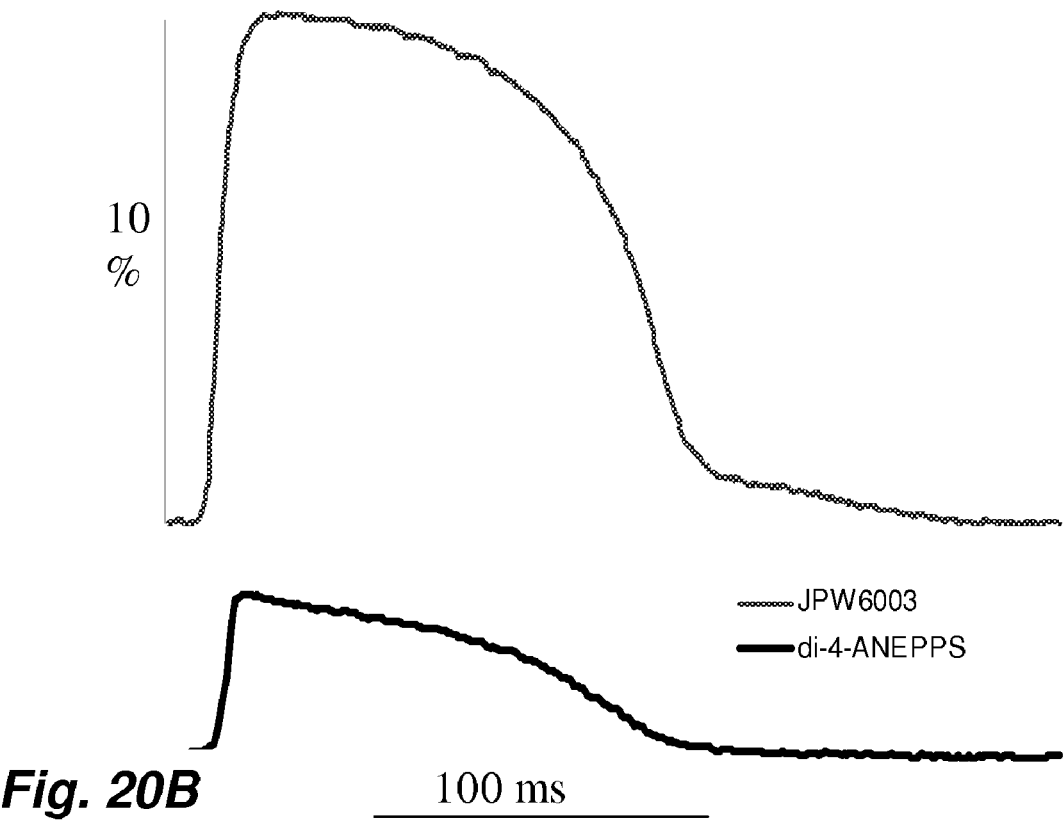
FIG. 20B depicts an illustration of experimental data acquired with respect to the various fluorescing chemical probes with respect to the present invention.

FIG. 20 depicts the fluorescence response of the class B fluorescing chemical probe 200, JPW 6003, in various cardiac tissues. In FIG. 20A, the very bottom trace shows the performance of di-4-ANEPPS in rat for comparison with the class B dye JPW 6003. Further traces from bottom to top correspond to rat, guinea pig, pig, and transillumination mode in pig, respectively. The measurements were taken of tissue perfused by Tyrode's solution. In FIG. 20B, the bottom or lower trace shows the performance of di-4-ANEPPS, while the upper trace shows the performance of the class B JPW 6003 probe in a blood-perfused pig tissue.

FIG. 21 shows fluorescing chemical probe 200 loading and washout dynamics in a subject rat. FIG. 21A and FIG. 21B each show the dynamics for the normalized total fluorescence, and voltage-sensitive fluorescence ΔF/F, respectively. The dynamics of the dye di-4-ANNEPPS is shown in both FIG. 21A and FIG. 21B for comparison. Also, the error bars in the FIG. 21A show the level of data variation. All curves in FIGS. 21A and 21B are averages of 3 to 5 experiments.

FIG. 22 shows dye (fluorescing chemical probe 200) loading and washout dynamics in blood-perfused pig heart. The three curves show dynamics of the normalized OP amplitude, normalized total fluorescence, and voltage-sensitive fluorescence ΔF/F (also referred to as delta F/F). FIG. 22 A depicts dye loaded in Tyrode solution, which later was switched to blood at the time moment shown by the arrow in FIG. 22A. FIG. 22B depicts the dynamics of the dye loading through direct injection into blood flow, which is shown for comparison to FIG. 22A.

The JPW dyes of class A and class B, or the functional equivalents thereof, with various R groups on the generic JPW' class A and class B molecules may be used in conjunction with the method of optical electrophysiological probing 100. Though the dyes presented herein include structural similarities, it is herein noted that one or more dyes may likewise be used in the method, provided the dyes share or are similar to the desirable characteristics, features, and functions of the dyes disclosed herein in a manner such that they may be accorded into the embodiment of the present method 100.

For example, the JPW class B voltage sensitive dyes of the present invention may be classified according to some of the various properties that they exhibit with respect to dye imaging. For example, the JPW 6003 dye may show delta F/F values of approximately 20% in a cell membrane of a target thick target tissue (thickness at about 10 mm), in which delta F/F is essentially the dye's fluorescence emission value or fluorescing intensity. In blood-perfused cardiac tissue, the dye may exhibit characteristics of 12% for delta F/F values at about 10 mm thickness.

The method of optical electrophysiological probing 100 may further comprise the step of contacting a thick portion of tissue with said fluorescing chemical probe to create a thick portion of treated tissue 120. Thick tissue may refer to tissue that is approximately a few millimeters thick to tens of millimeters thick. For example, a portion of thick tissue 70 may be from about 2.0 mm thick to about 20 mm thick, such as about 15 mm thick for example.

Contacting a thick portion of tissue, as used herein, may refer to one or more of the methods of applying the fluorescing chemical probe 200 to a portion of thick tissue without penetrating the portion of tissue that is to be optically probed by the method 100. Contacting may be selected from the group consisting of: close-proximity injecting, diffusing, circulating, topically applying, and combinations thereof as may be used in the art. Therefore, an example of contacting may include injecting the fluorescing chemical probe 200 into a portion of tissue from which it will diffuse, circulate, or otherwise transfer to the portion of tissue referred to as the treated portion of tissue.

As another example, contacting a thick portion of tissue may include applying the dye to the interior or exterior of the tissue or organ to be probed, such that through cohesion, adhesion, and diffusion, the fluorescing chemical probe 200 may be passively transferred through the portion of tissue to a given depth, or to the other side of the tissue thereby completely treating a cross-section of tissue.

As still another example, contacting may include injecting or otherwise distributing the dye into the circulatory system of a subject that in turn circulates the dye to the appropriate portion of thick tissue. Likewise, as yet still another example, contacting may include injecting the dye into a space, including, for example, a chamber of a heart such that the dye is in close proximity to the walls and/or surface of the tissue and may be diffused therethrough. Also, it should be noted that when the organism's body may be opened with surgical applications, the dye may be administered topically either with or without additional additives, including a medicament to aid in treating a medical symptom or diagnosis, or a diagnostic agent to aid in the assay or other determination of a heart or tissue condition or illness.

A thick portion of treated tissue 75 may refer to the area of tissue that has been contacted with the fluorescing chemical probe 200 and thereafter substantially retains a concentration of the fluorescing chemical probe 200 for at least a minimal amount of time prior to internalization (wash out). A thick tissue may be, for example, about 2 millimeters thick, about 5 millimeters thick, about 10 millimeters thick, or about 20 millimeters thick.

It should be noted that the step of contacting a thick portion of tissue 70 with said fluorescing chemical probe 200 to create a thick portion of treated tissue 75 may be facilitated by combining the fluorescing chemical probe 200 with one or more diluents, adjuvants, solvents, or delivery agents. Alternatively, the dye may be in a pharmacologically acceptable salt form to facilitate delivery into a targeted thick portion of tissue 70 and biocompatibility.

For example, the solid fluorescing chemical probe 200 may be dissolved in dimethylsulfoxide (DMSO) to make a solution of dye. For example, the fluorescing chemical probe 200 stock solution may comprise a 10-50 microMolar stock solution, which may in turn be kept under argon purge, vacuum sealed, stored at low temperature, or kept frozen until ready for use in the exemplary embodiment of the method 100. The fluorescing chemical probe 200 DMSO stock solution may be injected, imbibed, or otherwise contacted to the thick portion of tissue. For example, the dye solution for injection may be made by dissolving a portion of stock solution into a portion of Ringer's solution or Lock-Ringer's Solution (for example, several milliliters of Ringer solution). For example, Lock-Ringer's solution may comprise 140 millimoles/liter (mmol/l) NaCl, 5.6 mmol/l KCl, 1.0 mmol/l $MgCl_2$, 5.0 mmol/l HEPES, 10.0 mmol/l Glucose, 2.0 mmol/l $NaH_2PO_4$ and 2.2 mmol/l $CaCl_2$.

Also, to facilitate contacting of the fluorescing chemical probe 200 to a portion of thick tissue, Pluronic F-127 may be added to the final concentration of stock solution and Ringer's or Locke-Ringer's solution. Pluronic F-127 is an FDA approved loading agent that may typically be used for loading dyes like di-4-ANEPPS. For example, Pluronic F-127 may be added to the final concentration at about 0.1% to about 1.0%, more specifically, about 0.2 to about 0.5%. As other examples of diluents, ethanol may be utilized. Alternatively another loading agent similar to F-127, may be utilized. Alternatively, cyclodextrins may be utilized, including for example gamma cyclodextrin. While cyclodextrins may be used to encapsulate the dyes and increase solubility, the encapsulation itself may lower the effective delivery of the dye to the subject tissue.

Contacting a thick portion of tissue with said fluorescing chemical probe 200 may be done with various dye concentrations. For example, the dose of JPW 6003 or JPW 6033 dye may be on the order of about 1 to 10,000 nanomoles. As another example, the dose of JPW 6003 and 6033 may comprise about 10 to about 100 micromoles. As still yet another example, the fluorescing chemical probe 200 may be contacted to a portion of thick tissue 70 at a concentration of about 100 nanomoles per 1 gram of cardiac tissue.

After the step of contacting with a fluorescing chemical probe 200 to yield a treated portion of thick tissue 120, the method of optical electrical physiological probing 100 may comprise applying a first range of wavelengths of electromagnetic radiation to said treated portion of tissue 130.

Applying electromagnetic radiation 230 having a first range of wavelengths may refer to administering through a light source including a visible light source, laser, or other means to bring the first range of wavelengths 230 into contact with the treated portion of thick tissue 75 such that the electromagnetic radiation having the first range of wavelengths 230 may be absorbed by the tissue and by the fluorescing chemical probe 200 that is diffused therein.

The light source may be, for example, a light source that may generate and administer red visible light. As another example, a laser light source may generate and administer near infrared electromagnetic radiation, infrared electromagnetic radiation, or far infrared electromagnetic radiation onto the thick portion of treated tissue such that the tissue and dye may absorb the radiation applied. For example, light from a tungsten lamp may be sent through a monochromator and focused onto the surface of a thick portion of treated tissue 75 or a model of a hemispherical lipid bilayer stained with a fluorescing chemical probe 200. In vivo, the tissue, such as heart tissue, may have voltage potential changes across the cells, in milliVolt detectable ranges. In a model system, a train of voltage steps may be incorporated, for example ±50 mV voltage steps may be applied to the membrane at a frequency of 40 Hz. Then, the modulation of the detected light signal (plurality of emitted wavelengths) may be measured with a lock-in amplifier.

It should be noted that due to the advantageous properties class A and class B fluorescing chemical probes, and their excitation ranges of wavelengths which are significantly shifted from the band at which tissue and blood absorb, visible red light, near infrared light, and infrared light may be utilized with this embodiment of the present invention. As such, the level or intensity of light or electromagnetic radiation which may be required to acquire an acceptable image and/or reading is much lower than the light intensity needed with the di-4-ANEPPS dye of the same class. That is, the intensity of excitation light may be, on average, seven to ten orders of magnitude lower with various embodiments of the present invention. This may be, for example, because there is much less scattering and noise with the excitation and emission wavelengths or wavelength bands as both are shifted from the bands at which biological tissue and materials absorb light. As a result, the light source, illumination source, and/or laser source may operation at a much lower intensity and still yield a much higher quality image.

The first range of wavelengths of electromagnetic radiation 230 may be selected from those wavelengths or like band of wavelengths which may have a correlation to a wavelength, more than one wavelength, or a band of wavelengths at which the excitation wavelength 222 of fluorescing chemical probe 200, and likewise, the treated portion of tissue 75 may become excited and emit at least a detectable quantity of fluorescing electromagnetic radiation. This may be at a maximum excitation wavelength, or a notable and measurable excitation wavelength, such that cost, ease of administration (e.g. biocompatibility, retention time, and fluorescing intensity) are maximized with respect to economics, efficiency, effectiveness, and practicality. That is, because the probes typically have excitation bands including a range of wavelengths, it is possible to select a lower cost or available light source that may excite the dyes within its excitation band, though not at its wavelength of maximum absorption. As such, the first range of wavelengths 230 of electromagnetic including said of said fluorescing chemical probe 200 may be measurable and distinguishable (part of the excitation band) and therefore practical for use with this embodiment of the present method 100, although not exactly at the lambda max values for the fluorescing chemical probe 200.

After the step of applying a first range of wavelengths 130, the method of optical electrophysiological probing 100 comprises detecting a plurality of depth-specific emission wavelengths emitted from said thick portion of treated tissue, said plurality of depth-specific emission wavelengths incremented from a surface of said thick portion of treated tissue to an inner tissue depth of at least about 2.5 millimeters 140.

Detecting may be done with various types of detectors, including fiber optic devices, photodiode arrays, digital cameras, and/or visual inspection. For example, the use of detectors, including, for example, high-speed video cameras or photodiode arrays may yield high spatial and temporal resolution recordings of electrical activity in the layers of cardiac tissue. Also, these types of detectors may permit visualization/observation and recording of, for example, complex structures including spiral waves.

The detector may be set up such that it is on the same side of the tissue as the light source, such that the detection is done through a reflection of light technique. Also, the detector may be set up on the opposite side of the tissue from the light source, such that the detection is done through a transillumination of light technique. Also, there may be more than one detector set up such that both reflection and transillumination methods simultaneously collect data. That is, in transillumination mode, the excitation source (illumination device) and an emission detector (detector) may be on substantially opposing sides of a thick portion of treated tissue. One or the other method may be preferred based on differing scientific and experimental variables.

The plurality of depth-specific emission wavelengths 240 emitted from said thick portion of treated tissue 75 may refer to more than one emission wavelength 240 which is emitted from the thick portion of treated tissue 75. As the fluorescing chemical probe 200 is comprised of a plurality of molecules, after the molecules diffuse into the portion of thick tissue 70 to yield a treated portion of thick tissue, molecules of the fluorescing chemical probe 200 at different levels of thickness may likewise be excited by the application of a first range of wavelengths 230 including at least a portion of the excitation wavelength 210. In such a manner, upon excitation of a treated portion of thick tissue, a plurality of depth-specific emission wavelengths 75 will be emitted.

Then, one may review the emissions in an incremented form such that, for example, there are available detailed emission wavelengths from an area of the treated portion in a cross-section, ranging from the surface 71 of said thick portion of treated tissue 75 to an inner tissue depth 76. The inner depth 76 may range from about a few microns from the surface 71 of the thick portion of tissue to about 15 millimeters. The incrementation may be on the molecular level, cellby-cell, layer-by-layer of tissue, one or more microns, one or more millimeters, or any other predetermined thickness determination method known to those in the art. The inner depth may be measured as a displacement from the surface of the treated tissue portion. For example, the inner depth of a thick portion of treated tissue may be at least about 2 millimeters. As another example, the inner depth of a thick tissue portion of treated tissue may be about 15 or 20 millimeters from the surface of the treated portion of tissue.

The method of optical electrophysiological probing 100 may further comprise the step of recording data relating to the plurality of depth-specific emission wavelengths 150. Once the plurality of depth-specific emission wavelengths 240 have been detected during the detecting step 140, the data therefrom (results) thereof may be recorded to create a permanent record of the readings for use in research, diagnostics, or storage on to one or more media storage devices which may be computer readable medium, or otherwise accessible with one or more electronic devices. The various types of computer readable media and electronic devices that may be used in conjunction with this exemplary embodiment of the method 100 of the present invention may be disclosed and discussed infra with respect to the discussion of an aspect of the present invention detailing a system.

The method of optical electrophysiological probing 100 may further comprise analyzing the plurality of depth-specific emitted wavelengths to determine an at least one physical parameter 160. Analyzing may include correlating, calculating, measuring, diagnosing, characterizing, deriving, or otherwise determining at least one physical parameter. The analyzing step may be done, for example, by a clinician, a physician, a researcher, a technician, or other person, termed a "user", of knowledge and skill in the art to correlating, calculating, measuring, diagnosing, characterizing, deriving, or otherwise determining at least one physical parameter. Also, the user may complete the analysis step in combination with a computer system. Alternatively, the computer system may correlate, calculate, measure, diagnose, characterize, derive, or otherwise determine at least one physical parameter completely with proper programming and/or software, which may then be either stored, presented, or stored and presented to a user. The user may then base a diagnosis, treatment plan, or one or more variables on the at least one physical parameter.

The at least one physical parameter may refer to a single physical parameter variable, which may be measured once, or a plurality of times over a length of time or cycle, or a plurality of various physical parameters which may be measured either once or a plurality of times over a length of time or a cycle. The at least one physical parameter may be, as previously disclosed, one of more differing variables of a subject's thick portion of treated tissue. For example, one or more of the physical parameters may be selected from the group consisting essentially of: a tissue health, an electrical potential, a thickness, an emission wavelength intensity, a two-dimensional model, a three-dimensional model, a computational model, a cross-sectional model, a disease characteristic, a diagnostic condition, a symptom, a blood perfusion, circulation, effectiveness, a molecular event, a disease progression, a high-resolution cross-sectional image, and combinations thereof.

A tissue health may refer to how well a tissue, for example, a cardiac tissue, conducts voltage and exhibits membrane potentials across one or more areas, how well a dye is absorbed into the tissue, and if the tissue has one or more defects in it which may be readily ascertained by the absorption or non-absorption of the fluorescing chemical probe 200.

An electrical potential may refer to the ability of a tissue, including for example a heart tissue, to readily conduct voltage that is needed in order to create an impulse through the cardiac tissue to initiate the heart muscle to contract and cause the heart to beat. The fluorescing chemical probe 200 may be essentially a voltage-sensitive dye such that the probe will only fluoresce at points where it has absorbed into the membrane of a cell that is exhibits a change in electrical potential. A thickness may refer to understanding the measurement of a cross section of a treated portion of thick tissue at various points in order to understand how the various cells of the tissue may be aligned near one another, including location of tissue bundles, blood vessels feeding the cardiac tissue with oxygen, etc. The emission wavelength intensity may refer to the level of fluoresce that may be detectable or otherwise observed from a thick portion of treated tissue which has been excited with a first wavelength of electromagnetic radiation including the excitation wavelength, thereby exhibiting a fluorescing emission wavelength. The intensity may further refer to a comparative analysis between one area's intensity and another area's intensity, where area may refer to various points of a treated portion of thick tissue that is exhibiting a detectable or observable amount of emission wavelength of, for example, a fluorescing-type character. A computational model may include, for example a two-dimensional model, a three-dimensional model, a cross-sectional model of a portion of thick treated tissue or the entire organ, for example a heart. A disease characteristic may include, for example, low intensity of fluorescing emission wavelength in one or more areas. A diagnostic condition may include, for example, a screening of a subject's treated portion of tissue to determine if one or more variables exist. A symptom may refer to a physical parameter that may be indicative of a disease, a condition, or suggest a need to perform one or more diagnostics on one or more thick treated portions of tissue. Other physical parameters may include, as previously disclosed a blood perfusion, circulation, effectiveness of heart as a pump, a molecular event, including an electrical impulse or change in membrane potential, a disease progression, a high-resolution cross-sectional image, and combinations thereof. It should also be noted that the physical parameter may be a function of the subject (organisms), age, weight, height, body surface area, or relative condition of the subject's heart.

The method of optical electrophysiological probing 100 may further comprise administering a second range of wavelengths of electromagnetic radiation to said thick treated portion of tissue after a predetermined period of time 170. The second range of wavelengths of electromagnetic radiation 250 may be the excitation wavelength of the fluorescing optical probe 200, or a band of wavelengths in which the intensity of fluorescing from the treated portion of thick tissue may be observable or detectable. Administering the second wavelength 170 may be equivalent to applying a first wavelength 130, yet at a different predetermined time of administration. For example, there may be a predetermined passage of time between applying the first wavelength and administering the second range of wavelengths, for example, such that the two wavelengths define a treatment plan, screening plan, or diagnostic of a thick portion of treated heart tissue. Also, the method of optical electrophysiological probing may be configured such that the first range of wavelengths of electromagnetic radiation and a second range of wavelengths of electromagnetic radiation are both of different intensities of electromagnetic radiation or different beam sizes. Further, the first range of wavelengths of electromagnetic radiation and a second range of wavelengths of electromagnetic radiation may comprise partially overlapping or completely different ranges of electromagnetic radiation. This may be helpful, for example, in procedures in which different classes of dyes may be co-administered, wherein the dyes may have a slightly overlapping or different range of wavelengths in which an excitation wavelength or range of wavelengths lies. Also, one or more of the steps of the method of optical electrophysiological probing may be reiterated once, twice, or more.

Figure 6:
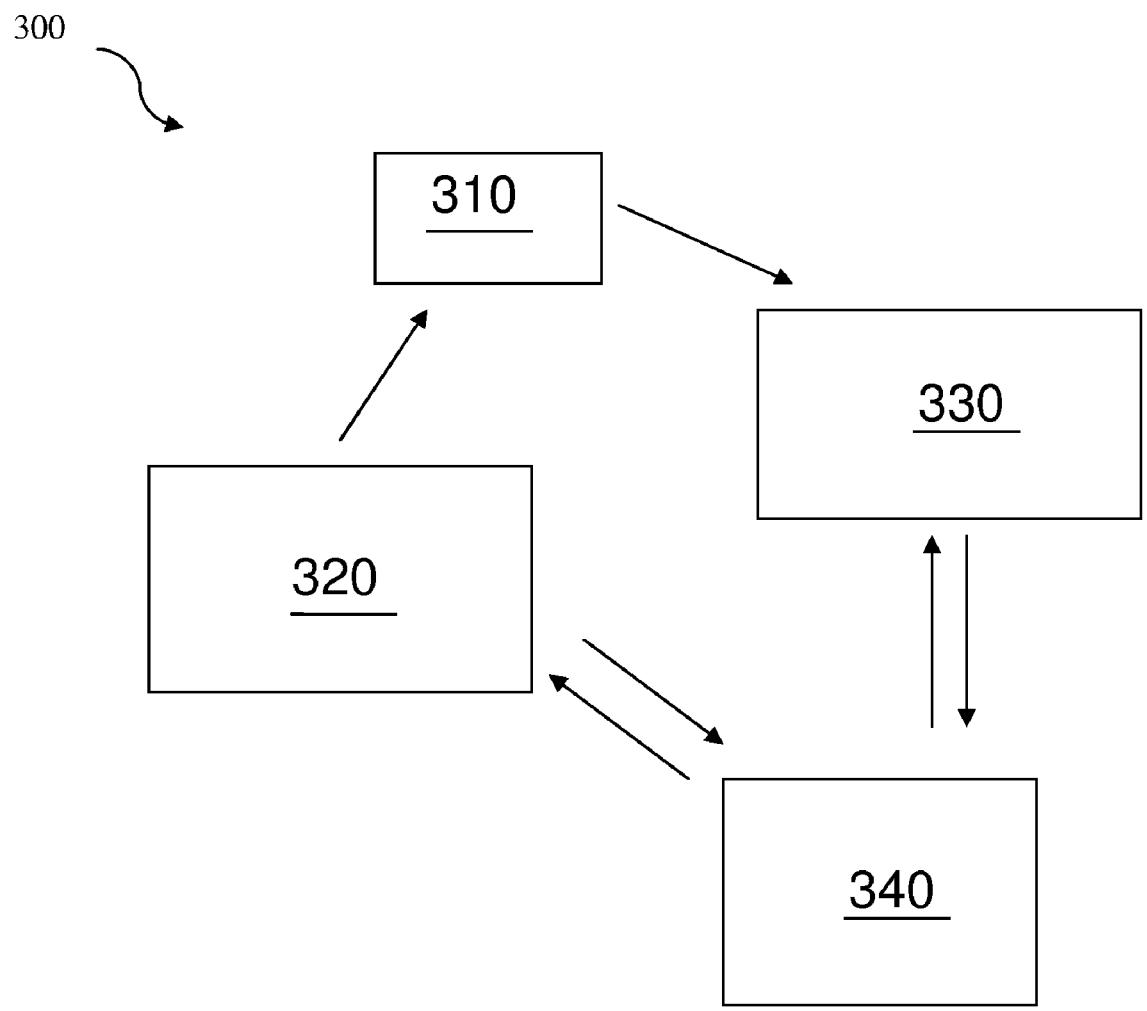
FIG. 6 depicts an example of an embodiment of the system of the present invention.
Figure 7:
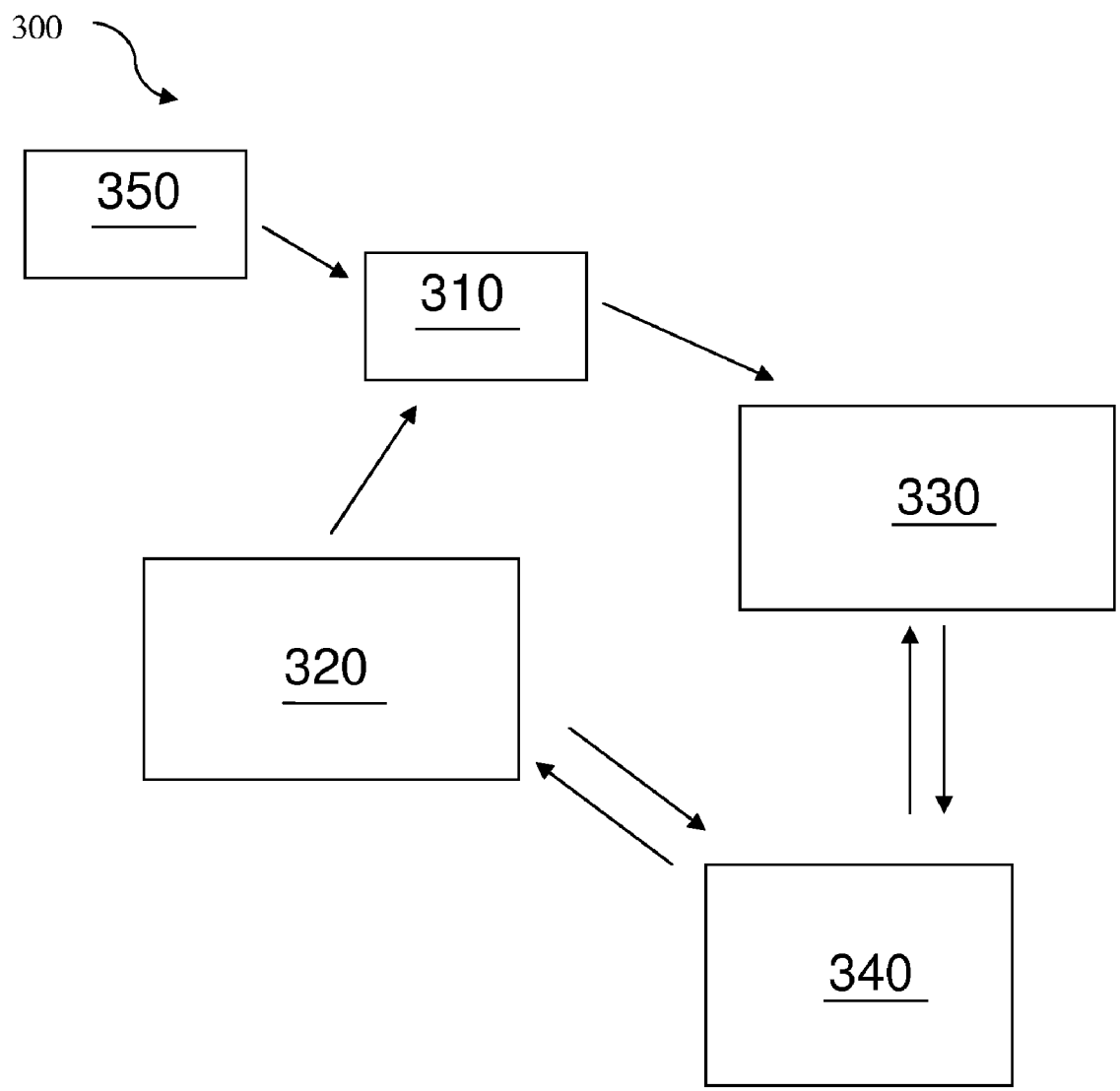
FIG. 7 depicts another example of an embodiment of the system of the present invention.

Another aspect of the present invention may be a system of in-depth in vivo imaging. The system of in depth in vivo imaging 300 may comprise: a dosage of a styryl probe, an illumination source, and a photodetector. The system of in depth in vivo imaging 300 may also comprise a computer system. The elements and features of an example of an embodiment of the system of in depth in vivo imaging 300 may be discussed below, with reference to FIG. 6 through FIG. 8.

The system of in depth in vivo imaging 300 may comprise a dosage 310 of a fluorescing chemical probe 200. The styryl probe may be, for example, class A or class B voltage-sensitive dyes of one of the formulas previously discussed, or otherwise similar to the aforementioned dyes with respect to structure of operability in the defined and described system. The fluorescing chemical probes 310 may be characteristic in that said probe has an excitation wavelength 210 and an emission wavelength 220, said excitation wavelength 210 differs by at least about 90 nanometers or more from said emission wavelength 220. This difference in wavelengths of the excitation and emission wavelengths may be more commonly referred to as a Stokes shift.

A Stoke's shift may refer to the difference (in wavelength units) between positions of the band maxima of the excitation (absorption) and emission spectra in, for example, fluorescing species which may be configured to be biologically compatible to a subject tissue. A large Stokes shift (i.e., the difference between the excitation and emission wavelengths) may make them particularly convenient for microscopy, because a large Stokes shift eases the exclusion of scattered and reflected light and the filtering away of background autofluorescence. Also, the fluorescing chemical probe 200 may have a low level of toxicity, referred to generally as biocompatibility.

The illumination source 320 of the system may refer to a light source 322 or laser source 324 which may provide electromagnetic radiation of or including the excitation wavelength 210 of a range of wavelengths for the fluorescing chemical probe 200. The illumination source 320 may be further configured to illuminate a dosed portion of subject tissue 78.

The photodetector 330 of the system 300 may refer to a photodiode array 320, a charge coupled device camera 330, high-speed camera, or similar device. The photodetector 330 may be configured to detect a plurality of emission wavelengths 245. The emission wavelengths 245 may be readings from a surface of said subject tissue 72 to a predetermined tissue depth 76 of at least about 2.5 millimeters of tissue depth. The readings may be recovered and sorted in an incremented fashion.

The system 300 may further comprise a computer system 340. The computer system 340 may be configured to collect and record said plurality of emission wavelength 245 from said surface of subject tissue 72 to the predetermined tissue depth 76. The computer system 340 may be disclosed and described with reference to FIG. 8 and the following paragraphs.

The computer system 340 may comprise, for example, a processor and a computer readable memory unit coupled to the processor, said memory unit containing instructions that when executed by the processor implement a method. The method may comprise the method for optical electrophysiological probing for tissue 100, including heart tissue. Alternatively, the method may comprise a method of screening a subject for a heart disease or condition, a method of diagnosing said physical symptoms as one or more heart diseases or conditions, a method of monitoring drug delivery and efficacy to tissue, including heart tissue, and/or a method for monitoring a user's heart effectiveness upon modification of one or more variables, including oxygen level, blood pressure, ineffective tissue (no electrical potential across a cell's membrane), etc.

An example of an embodiment of the computer system 340 of the present invention may provide a process for supporting computer infrastructure, said process comprising providing at least one support service for at least one of creating, integrating, hosting, maintaining, and deploying computer-readable code in a computing system, wherein the code in combination with the computing system is capable of performing a method. For example, the computer system may be capable of performing an optical electrophysiological probing method of 100 of the present invention, similar to the previous exemplary embodiment disclosed.

The computer system 340 comprises a processor 341, an input device 342 coupled to the processor 341, an output device 343 coupled to the processor 341, and memory devices 344 and 345 each coupled to the processor 341.

Input device 342 may be, inter alia, a keyboard, a mouse, a keypad, a touchscreen, a voice recognition device, a sensor, a network interface card (NIC), a Voice/video over Internet Protocol (VOIP) adapter, a wireless adapter, a telephone adapter, a dedicated circuit adapter, etc.

The output device 343 may be, inter alia, a printer, a plotter, a computer screen, a magnetic tape, a removable hard disk, a floppy disk, a NIC, a VOIP adapter, a wireless adapter, a telephone adapter, a dedicated circuit adapter, an audio and/or visual signal generator, a light emitting diode (LED), etc.

The memory devices 344 and 345 may be, inter alia, a cache, a dynamic random access memory (DRAM), a read-only memory (ROM), a hard disk, a floppy disk, a magnetic tape, an optical storage such as a compact disc (CD) or a digital video disc (DVD), etc. The memory device 345 includes computer code 347 which is a computer program that comprises computer-executable instructions.

The computer code 347 includes, inter alia, an algorithm used for mapping the electrical potential of organelles, cells, and tissues according to the present invention. The processor 341 executes the computer code 347. The memory device 344 includes input data 346. The input data 346 includes input required by the computer code 347. The output device 343 displays output from the computer code 347. Either or both memory devices 344 and 345 (or one or more additional memory devices not shown in FIG. 8) may be used as a computer usable medium (or a computer readable medium or a program storage device) having a computer readable program embodied therein and/or having other data stored therein, wherein the computer readable program comprises the computer code 347.

Generally, a computer program product (or, alternatively, an article of manufacture) of the computer system 340 may comprise said computer usable medium (or said program storage device).

Any of the components of the present invention may be deployed, managed, serviced, etc. by a service provider that offers to deploy or integrate computing infrastructure with respect to a process for system for electrophysiological probing of thick tissue of the present invention. Thus, the present invention discloses a process for supporting computer infrastructure, comprising integrating, hosting, maintaining and deploying computer-readable code into a computing system (e.g., computing system 340), wherein the code in combination with the computing system is capable of performing one or more methods of or related to the present invention.

Figure 8:
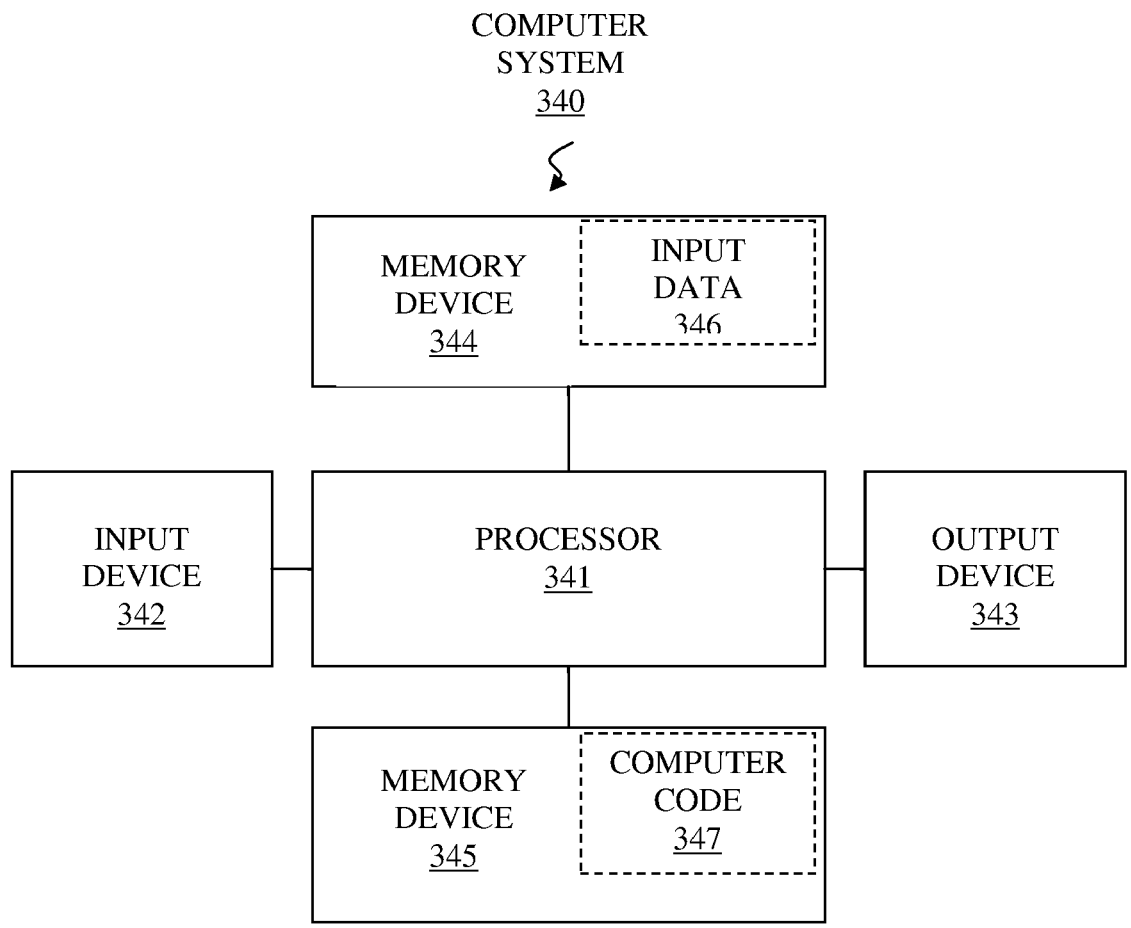
FIG. 8 depicts an example of an embodiment of the computer system of an embodiment of the system of the present invention.

While FIG. 8 shows the computer system 340 as a particular configuration of hardware and software, any configuration of hardware and software, as would be known to a person of ordinary skill in the art, may be utilized for the purposes stated supra in conjunction with the particular computer system 340 of FIG. 8. For example, the memory devices 344 and 345 may be portions of a single memory device rather than separate memory devices.

The system 300 may further comprise an administration member 370 for administering said dosage of said fluorescing chemical probe 200 to a subject tissue 70. The administration member 370 may comprise, for example, a transdermal patch, an intravenous line, a syringe, a bolous injection, a solution, a pill casing, and/or a topical application. The administration member 370 may be selected such that the administration means 370 conforms to the characteristics of the fluorescing chemical probe 200 and/or any solubilizing or delivery agents thereof to facilitate effective and efficient administration of the fluorescing dye probe 200 to a subject tissue 70.

Figure 9:
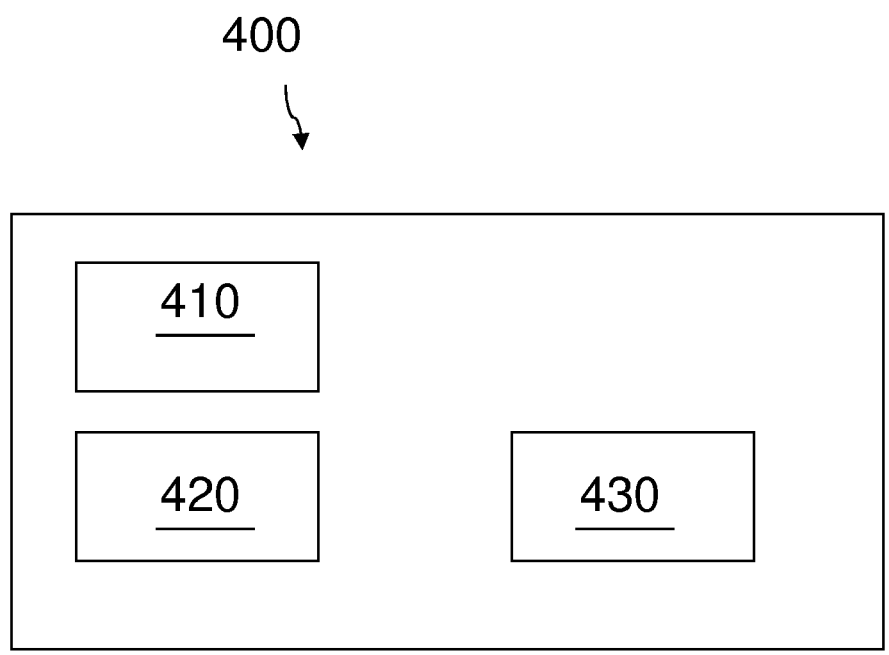
FIG. 9 depicts an example of an embodiment of the kit of the present invention.
Figure 10:
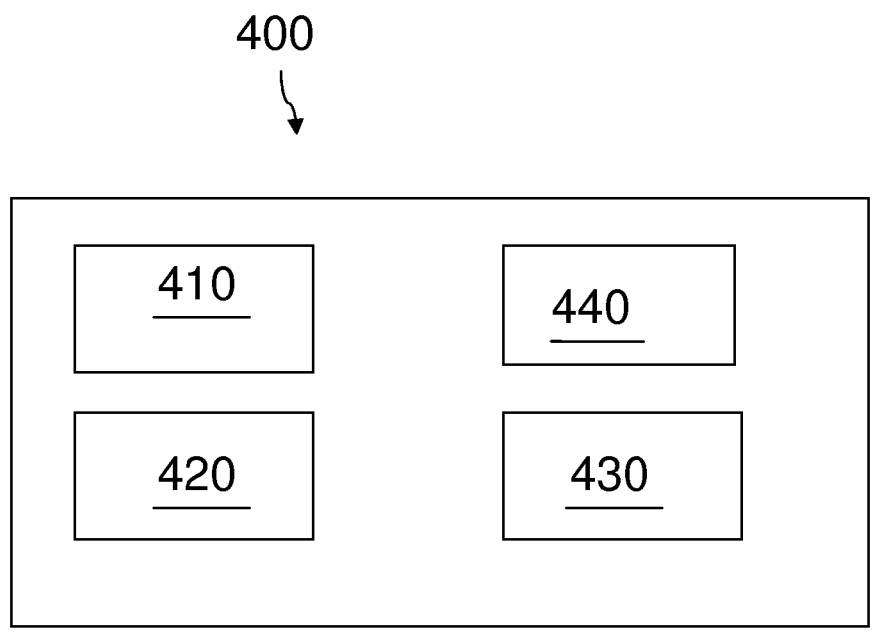
FIG. 10 depicts another example of an embodiment of the kit of the present invention.

A still yet another aspect of the present invention includes an optical probing kit for tissue 400. The optical probing kit 400 may be shown and described with reference to the paragraphs that follow as well as FIG. 9 through FIG. 10. The optical kit for tissue 400 may comprise, for example, a fluorescing chemical composition 410; an instruction 420; and a delivery member 430.

The fluorescing chemical composition 410 may refer to a fluorescing chemical probe 200 selected from one of those previously discussed which may be in combination with a delivery agent, solubilizing agent, or other material. This combination may facilitate dosing, biocompatibility, stability, solubility into a host organism or subject tissue, or otherwise create an ease of packaging, handling, and administration. The fluorescing chemical composition 410 may be configured such that the fluorescing chemical composition 410 may emit an electromagnetic radiation emission wavelength band from at least about 600 to about 1000 nanometers.

The optical probing kit 400 may further comprise an instruction 420. The instruction 420 may comprise a direction, dosing amount, or instruction for administering said fluorescing chemical composition 410 to a user or a subject tissue 70. The instruction 420 may be, for example, a relevant material safety data sheet, an instruction for mixing the dosage solution, a detailed listing of the side effects of taking the fluorescing chemical composition 410, the physical parameters that the fluorescing probe may measure, the treatment plan for administering the fluorescing chemical probe, the instruction for safely disposing of the non-utilized or left over fluorescing chemical compound 410, poison control phone numbers, manufacturer information, etc. That is, the instruction 420 may be one or more pieces of information which a user or subject may find helpful in administering the fluorescing chemical composition 410 to a thick portion of tissue 70 to be treated.

The optical probing kit 400 may further comprise a delivery member 430. The delivery member 430 may be configured to deliver said fluorescing chemical composition 410 into a portion of tissue. That is, the delivery member may comprise an apparatus by which the fluorescing chemical composition is injected, topically applied, internally applied, ingested, or otherwise circulated throughout the subject or organism to a subject thick portion of tissue to be treated by the kit 400. For example, the delivery member may comprise a syringe, a pipette, a transdermal patch, a pill, or combinations thereof.

The optical probing kit 400 may further comprise a computer program product 440. The computer program product 440, may comprise, for example, a computer usable medium having a computer readable program code embodied therein. The computer readable program code may, for contain, for example, instructions that, when executed by a processor of a computer system, implement a method for manipulating the data acquired through administration and illumination of said fluorescing chemical composition 410 in a user or subject's tissue, including heart tissue The computer software program 440 of an example of an embodiment of the present invention may allow a user, including a clinician, a technician, a researcher, a student, a physician, and/or a professor to collect, manipulate, and analyze one or more readings that may be acquired with the kit. The computer software program may allow a user to create one or more of the following, including: a three dimensional model of at least a portion of a user's tissue, a two dimensional image of at least a portion of a user's tissue, a cross-sectional image of a user's thick portion of tissue, or a physical parameter of a subject or thick portion of treated tissue, said physical parameter a single measurement, a plurality of measurements, or plurality of measurements with respect to time, drug administration, progressing symptom, etc.

As still yet another aspect of the present invention comprises an optical mapping and signal measuring composition 250. The electrophysiological measuring composition 250, may comprise a voltage sensitive dye of the following formula:

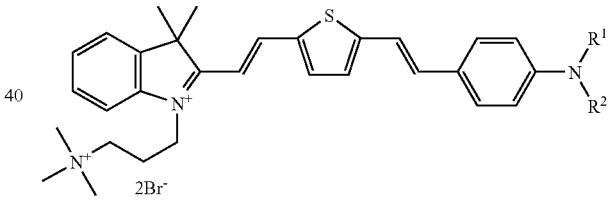

That is, the electrophysiological measuring composition 250 may comprise one or more voltage sensitive dyes selected from the group consisting of class A JPW dyes. That is, based on the JPW class A generic structure above, R1 and R2 may be selected from many various chemical functional groups. For example, R1 and/or R2 may be selected from various hydrocarbon groups, including alkyl groups, alkenyl, alkynyl, benzyl, and phenyl groups. Also, the R1 and R2 may be made up of one or more other functional groups, though, for example, hydrocarbon groups attached at the tertiary amine sites may generally increase solubility in a biological host or model. Therefore, R1 and R2 may be each independently selected from the groups consisting of methyl, ethyl, butyl, propyl, pentyl, hexyl, heptyl, octyl, nonyl, and decyl alkane functional groups. Alkyl groups of a chain length may associate to a cell membrane very easily, thereby increasing the dyes solubility and overall sensitivity. Alternatively, although a thiophene is used as a junction linker in the chromophore, other heterocyclic compounds may also be utilized, for example, furan. In the class A compound of the present invention, R1 and R2 may be the same functional group. For example, R1 and R2 may be methyl groups, as is the case in, for example, JPW 3067. As another example, R1 and R2 may be butyl groups, as is the case in, for example, JPW 5020. As still another example, R1 and R2 may be octyl groups, as is the case in, for example JPW 5034. Alternatively, R1 and R2 may be different groups, with different sizes, sterics, and or characteristics such that R1 and R2 may collectively allow the compound 250 of the present invention to associate and or otherwise affiliate with one or more cells.

Further to the embodiment of the electrophysiological measuring composition 250, the composition may further comprise a delivery agent 260. The delivery agent 260 may be at least one of a physiologically acceptable adjuvant, solvent, or diluents. For example, the delivery agent may comprise pluronic F-127, cyclodextrin, gamma cyclodextrin, dimenthylsulfoxide (DMSO), ethanol, or combinations thereof.

As the probes are used in each aspect of the various embodiments and examples of the present invention, as a preliminary matter, the relevant synthesis and characterization of the dyes is variation of polar groups can be used to optimize properties such as dye penetration and persistence, or voltage-sensitivity. It should be noted that the dye sensitivity is very high in both class A and class B materials. Further dye sensitivity is dependent upon the signal to noise level which may be achieved in measurement. The lower range of the probes for a processed signal may be 0.1 mV. This may correspond to a signal to noise ratio (processed) of 1000. The upper limit or range in which the probes may detect voltage is limited to the amount of voltage that may typically break down the dye molecule, which may typically be around a few to several volts. The other issue which may affect voltage-sensitive dye sensitivity is linearity between measured voltage and optical signal, which, in the present invention, the linearity may hold up under conditions of 500 mV.

The novel probes provide, for example, improved performance in terms of loading, internalization, washout and membrane-voltage-sensitivity. This may in turn enable various new experiments to be completed in the area of deep tissue probing of blood perfused tissue, which includes the examples and embodiments of the various methods and systems disclosed and discussed herein. Also, this may enable more efficient double-dye optical mapping (Ca/Vsub.m). Also, the particularly effective fluorescing chemical probes may be utilized in the field of cardiac electrophysiology, where the probes may provide sub-millisecond temporal resolution, high fluorescing, stable staining, low photobleaching, and low toxicity. That is, the probes may be used in conjunction with various embodiments of the method, system, and kit of the present invention with respect to almost any type of tissue or even individual cells which exhibits changes in membrane potential. Besides applications in, for example, cardiac cells and tissues, additional applications may lie in the area of the brain and individual neurons.

The method, system, composition of matter, and kit may be used in order to effectively understand and collect the time-varying optical signal proportional to the membrane electrical potential in cells, tissues, or organs. Alternatively, it is possible to collect time-independent signal which may provide anatomical features of the tissue. Though anatomical feature collection may be completed at or near the surface of a subject tissue, deeper probing of the changes in membrane potential may be measured both in close proximity to the tissue surface as well as in deeper layers. For example, the various embodiments of the probes, method, system, and kit of the present may be used in order to collect optical signals in deep tissue, up to 5 or even 7 millimeters in depth. For even deeper readings, including up to and over 10 mm thickness, it may be necessary to independently collect signal (fluorescence emission wavelengths) from both sides of a subject tissue. For this reason, more than one detector may be placed on either side of the subject tissue to record data accordingly.

Another application of utilizing the voltage sensitive dyes, including the fluorescing chemical probes may include, for example, accessing membrane potentials in cell population measurements with a spectrofluorometer or determine spatial patterns of voltage distributions associated with tissues, individual cells, or organelles.

Another favorable feature of the styryl dyes is their high fluorescence quantum efficiency when bound to membranes but negligible fluorescence in aqueous solution; thus only stained cells contribute to the fluorescence signal even if the experimental protocol does not permit washing away the staining solution. The existing repertoire of styryl potentiometric dyes has varying solubility, lipid avidity, tissue penetrability, and ionic charge that allows them to be customized for specific types of experimental demands.

The applications of the embodiments of the present invention extend to investigating spiral and scroll waves in millimeter thick layers or across whole ventricular wall (thickness up to ~10 mm), with the final goal being to reconstruct 3D scroll waves. As the fluorescing chemical probes provide lower light scattering and less background fluorescence, the probes may be utilized in investigating the spiral and scroll waves in millimeter thick layers across, for example, and entire ventricular wall. The entire ventricle wall may be, for example, up to about 10 mm thick to about 15 or 20 mm thick.

The transillumination method, as previously discussed, as well as narrow illuminating beam scanning and transmitted light recording may be used in combination with the embodiments of the present invention with respect to deeper imaging. Thus, in real biomedical applications, the novel probes, system, kit, and method of the present invention may show many advantages over the existing blue-red repertoire of voltage sensitive dyes. Some of these advantages may include, for example, greater depth of imaging, compatibility with blood perfused samples, and prolonged retention. Also, though the dyes may be structurally similar, differences in the dyes may cause differences including, for example, solubility in lipids, tissue penetrability, and ionic charge. These various factors may provide the opportunity to customize dyes for use in one or more types of environments or specific applications. Additionally, optical mapping techniques for blood-perfused cardiac tissues may allow the study of many specific features of an in vivo heart, including ventricular fibrillation (VF) baseline.

Experimental Data, Including Examples

JPW 6003, JPW 6033

Methods: Dye Spectra and Sensitivity Measurement in Model Membranes.

Voltage-dependent spectra in model membranes were measured by a voltage-clamped hemispherical lipid bilayer (HLB) apparatus modified for near infrared fluorescence detection. In this experiment, light from a tungsten lamp is sent through a monochromator and then focused onto the bottom of the HLB, stained with dye from the external aqueous bathing solution. The monochromator is then scanned over the wavelength range of interest while a train of ±50 mV voltage steps are applied to the membrane at a frequency of 40 Hz and the modulation of the detected light signal is measured with a lockin amplifier. The transmitted light signal is collected at 180° from the incident light. Fluorescence is collected at 90° via fiber optic light guide through cutoff filters at 715 nm.

Cardiac Tissue Preparation and Staining Methods

The dye testing experiments were performed on typical model animals: mice (n=6), rat (n=11), guinea pig (n=6), pig (n=13). All experimental protocols conformed to the *Guide for the Care and Use of Laboratory Animals* and were approved by the Committee for the Humane Use of Animal of the SUNY Upstate Medical University. Mice (C57BL/6, 20-25 g) were injected with ketamine (200 mg/kg IP), rats (Sprague Dawley, 300-400 g female) and guinea pigs were injected with heparin (550 U/100 g), and euthanized by sodium phentobarbital (1 ml/100 g for rats and 0.75 ml/100 g for guinea pigs). The heart was then immediately excised and placed in ice-cold cardioplegia solution (CPS) composed of (in mmol/l) 280 Glucose, 13.44 KCl, 12.6 $NaHCO_3$, 34 Mannitol. After removal of extraneous tissues, the aorta was cannulated and Langendorff perfusion was started with a standard oxygenated Tyrode's solution (composed of (in mmol/l) 130 NaCl, 24 $NaHCO_3$, 1.2 $NaH_2PO_4$, 1.0 $MgCl_2$, 5.6 Glucose, 4.0 KCl, 1.8 $CaCl_2$; buffered to a pH of 7.4) at 80 mm Hg and 36° C. Young pigs (15-20 kg,) were heparinized (500 IU, IV) and subsequently anesthetized with sodium phentobarbital (35 mg/kg IV). The heart was rapidly removed and Langendorff-perfused with cold (4° C.) CPS. The right free ventricular wall was quickly excised, and the right coronary artery was cannulated. Non-perfused tissue was removed, leaving a preparation of typically 5×5 cm and a thickness of 8 mm. The preparation was stretched on a plastic frame and perfused with a standard oxygenated Tyrode's solution at 80 mm Hg and 36° C. Whole cannulated heart (mouse, rat or guinea pig) or stretched pig tissue was put into special transparent chamber and superfused with the same solution at a rate of 30-40 ml/min. Perfusion and superfusion temperatures were continuously monitored and kept at 36±1° C. by using two sets of glass heating coils and heated-refrigerated circulators. Electrodes were sutured to whole hearts or inserted into pig tissue to monitor ECG. All preparations were continuously paced at the frequency 6.7 Hz, 5 Hz, 3.3 Hz and 2 Hz for mouse, rat, guinea pig, and pig, respectively.

Blood-perfused Langendorff preparation of pig heart was implemented. Briefly, approximately 1.5 liters of modified Tyrode's solution (37° C., composition in mmol/L: $Na^+$, 157; $K^+$, 4.7; $Ca^{2+}$, 1.5; $Mg^{2+}$, 0.7, $H_2PO_4^-$ 0.5, $Cl^-$ 137.6, $HCO_3^-$ 28.0, glucose 11.0, dextran 4% and insulin 10 U) was infused in an external jugular vein, and blood-Tyrode's mixture was collected at equal rate from a carotid artery. The heart was perfused with blood-Tyrode mixture in a Langendorff apparatus. The blood-Tyrode mixture will be oxygenated ($CO_2$ 5%/$O_2$ 95%), heated (37° C.) and filtered using a Liliput hollow fiber oxygenator (COBE Cardiovascular, Arvada, Co). Collector tubes were inserted into the right and left ventricles to collect all the blood coming out of the coronary sinus and Thebesian veins. Thereafter, the heart was "sealed" to ensure that all the outflow of perfused blood is collected for recirculation. The heart was placed in a warm bath with heated water-jacketed transparent glass wall and was superfused with an oxygenated, heated Tyrode solution. After a 20-30 min stabilization verified by a vigorous contraction and normal sinus rhythm, the excitation-contraction uncoupler diacetyl-monoxime (DAM) was added to the perfusate (15 mmol/l) to stop contractions. ECG was monitored throughout the experiment to ensure stable capture of the ventricles by the pacing electrode. In each experiment, 300 microL of the stock solution (18.8 mg/ml) of JPW6003 were mixed with 1 ml of the stock solution of Pluronic-127 (2 g in 10 ml DMSO) and dissolved in 30 ml of Tyrode's solution. For di-4-ANEPPS staining 40 microL of the stock solution (5 mg in 1 ml DMSO) was diluted in 40 ml Tyrode's solution to the final concentration of 10 μM. The dyes were injected directly into the aortic cannula during uninterrupted aortic perfusion.

After a 20-30 min stabilization period during which the perfusion flow and ECG was monitored, the excitation-contraction uncoupler diacetyl-monoxime (DAM) was added to the perfusate (15 mmol/l) to stop contractions of cardiac tissue. After a 20 minute equilibration, the preparation was stained by injecting voltage-sensitive dye solution into the perfusion flow (a bolus injection near cannula).

Solid dyes were dissolved in DMSO to make 10-50 mM stock solution that was kept frozen. The dye solution for injection was made by dissolving the required amount of the stock solution into 1-5 ml Ringer solution (composed of (in mmol/l) 140 NaCl, 5.6 KCl, 1.0 $MgCl_2$, 5.0 HEPES, 10.0 Glucose, 2.0 $NaH_2PO_4$ and 2.2 $CaCl_2$). To facilitate loading of JPW6003, pluronic F-127 was added at the final concentration of 0.2-0.5%. Various dye doses (1-1000 nmol) were administered, and optimal doses and concentrations were found by trial and error. 10-100 μM were found to be optimal dye concentrations, and 100 nmol per 1 g of cardiac tissue optimal doses of dye JPW6003. We used only up to 30% of these doses in the case of pig preparations because of much higher total dye consumption. It is recommended that dye loading (perfusion) be performed at lowered temperatures (32-36° C.) because of the tendency of the concentrated dye solution to evoke arrhythmias (ventricular tachycardia or fibrillation) immediately or a few minutes after dye injection at 36° C. The normal excitation wave propagation in cardiac tissue was verified by injecting a small amount of di-4-ANEPPS (3-10 nmol) both at the beginning and end of each experiment (using appropriate excitation/emission filters to prevent crosstalk between the dyes, as described below).

Optical Action Potential Recording

The optical setup for testing the new dyes was similar to the optical mapping setup described previously. Briefly, a collimated beam provided by a 250 W tungsten halogen lamp uniformly illuminated the epicardial surface of the preparation. The light was heat filtered and then passed through an excitation filter (520+/−40 nm for di-4-ANEPPS; 650+/−20 nm for the new styryl dyes). Optical action potentials (OP) were recorded with a cooled fast CCD camera (Little Jo by SciMeasure) with a Computar H1212FI lens (focal length 12 mm (6 mm for mouse heart), 1:1.2 aperture ratio; diameter 28 mm; CBC Corp), located at about 100 mm (20 mm for mouse heart) from the sample. Lenses of both the light source and camera were adjusted to illuminate and image a 25 mm in diameter area at the center of the preparation; hence spatial resolution in the images was 0.31 mm/pixel. The fluorescent light emitted by the voltage sensitive dye was isolated from excitation using 640±50 nm band pass filter for di-4-ANEPPS, or a 720 nm long-pass filter for the styryl dyes. The camera was located either on the same side of preparation for epifluorescence mode recording or at the opposite side for transillumination mode recording. To reduce cardiac tissue motion artifacts DAM was used as described above; whole rat or guinea pig hearts were additionally gently pressed against stretched nylon mesh (on a single side opposite to both light source and camera so as not to affect the amount of collected fluorescence). These measures in most cases completely eliminated motion artifacts.

Blood-perfused pig heart imaging was done in a similar way. Briefly, the dye was excited with a 400-watt tungsten-halogen lamp (excitation filter, 650+/−20 nm) and the fluorescence was collected above 715 nm using a Computar objective lens (HG1208FCS_HSP, F0.8, focal length 12 mm,) and externally cooled CCD camera (Dalsa CA-D1-0128T, Ontario, Canada) at the frame rate of 400-800 fps and 12-bit resolution.

The acquired images were offline processed to improve their quality. The background autofluorescence (endogenous fluorescence recorded under the same conditions before dye injection) was subtracted from each frame to obtain the voltage-dependent optical signal. To allow temporal alignment and subsequent averaging of successive paced action potentials, the trigger for the pacing stimulus was recorded as a single pixel in the movie frames. The alignment error was no more than one-half frame (~0.5 ms). We used ensemble averaging to improve signal to noise ratio (i.e., averaging the OP signals from 10-20 sequential recordings). To further reduce noise, the OP signal was low-pass filtered in both time (with 3-7 point triangular window, depending on the camera frame rate), and spatial domain (with pyramidal 5×5 kernel). The effective temporal and spatial resolutions were 1.76-3.33 ms and 0.78 mm, respectively. Dye loading and washout dynamics were assessed from averaged sets of OP recordings (3-5 specimens). To facilitate comparison, fluorescence and OP signals were normalized to their peak values (defined as the difference between maximum and minimum values) in some figures.

For the dye loading dynamics, the time to reach peak values of background fluorescence (membrane voltage independent component of the dye molecules fluorescence), OP, and ΔF/F were determined by simple visual inspection of the dynamic plots. For the dye washout dynamics, analogous half-times of the same parameters were determined.

Absorbance spectra were measured in ethanol (panel A), and a model membrane made of multilamellar lipid vesicles (MLV) composed of egg phosphatidyl choline (panel B). The absorbance spectra reveal single maxima that represent a high level of the dye purity and absence of different configurational isomers. The absorption maxima for JPW6003 in ethanol occurred at 603 nm. For the dye JPW 6033 all absorption maxima are shifted 20-40 nm to shorter wavelengths, but absorbance is 2-3 times higher. Though the long wavelength absorbance peaks range from 561 nm to 603 nm in ethanol, and 526 nm to 539 nm in MLV, in practical applications both dyes can be efficiently excited over a much broader range (500-700 nm), allowing one to optimize excitation for the dye in different tissues, including blood perfused tissue.

Improved Voltage Sensitivity and S/N Ratio JPW 6003, JPW 6033

The new dyes were found to perform efficiently in various cardiac tissues and provide OP 50-100% greater to those of di-4-ANEPPS. The most efficient dye, JPW6003 showed delta F/F=20% in a model membrane, and 18.7% in pig tissue. Also this dye performed very efficiently in thick cardiac tissue (~10 mm): in transillumination mode (when an excitation source and an emission detector are on opposite sides of tissue) JPW6003 showed delta F/F=20%. JPW 6033 showed slightly lower values, at least in part due to the use of excitation and emission filter sets that were found optimal for the dye JPW6003. The absorption and emission peaks for JPW6033 are shifted by 20-30 nm relative to JPW6003, so optimization of filter sets for JPW6033 may yield further improvement in its performance.

It should be noted that raw optical signals are quite noisy: signal to noise ratio of raw signals were 20-40. To obtain good quality it is necessary to apply standard noise reduction procedures such as accumulation of the periodic optical signal and spatiotemporal filtering. Though 10-20 sequential Ops were typically accumulated, if very detailed dynamics are not of primary interest, it is possible to accumulate an even larger number of OPs. It is well known that the noise level decreases as the square root of the number of accumulated samples. Spatiotemporal filtering allows further noise reduction by filtering out CCD camera noise, and possible vibrations of the tissue surface in the superfusion flow. These procedures allowed to increase signal to noise ratio to 500-1000.

Optical Mapping of a Blood-Perfused Tissue

The dye JPW6003 performed very efficiently, exhibiting rapid loading, high voltage sensitivity, slow washout, and slow internalization. The kinetics of dye loading in blood-perfused hearts was quite different from those perfused with Tyrode's solution. When the dyed was injected during recirculated-blood-perfusion there was a very slow increase in total fluorescence and OP (~1 hour) whereas delta F/F remained practically constant (at the level of 5-6%) after 2 min of injection. When the dye was loaded during Tyrode's perfusion (FIG. 7A), the initial loading was fast and delta F/F value has high (up to 12%), but return to blood perfusion caused a large gradual decrease in total fluorescence, OP, and delta F/F. Interestingly, the steady-state level of delta F/F during blood perfusion was similar (~5%) regardless whether the dye was injected during Tyrode's perfusion with subsequent blood perfusion or it was injected directly into the blood flow. A comparison of these two kinetics could be explained (quite speculatively) by a phenomenological model describing dynamic equilibrium between just two types of binding sites (pools) of the dye in the blood-perfused heart. One pool is obviously the membranes of excitable cardiomyocytes (the "active" pool). This pool should provide voltage-sensitive fluorescence with delta F/F~12% as measured in the absence of blood. The second pool (the "passive" pool) is associated with blood itself (possibly including blood cells and components of plasma). It fluoresces and increases the background but does not provide voltage-sensitive fluorescence, leading to the reduction in delta F/F from 12 to 5%. Thus, when the dye is injected in the blood flow, a significant portion of it is bound first to the "silent" pool. Then it is slowly released from the "silent" blood pool and is redistributed between the "passive" pool and the "active" pool. The system reaches a steady-state equilibrium yielding delta F/F ~5%. The same steady-state is apparently reached via a different route, when the dye in injected in the Tyrode's perfusion. In this case the only pool present is the "active" pool (cardiomyocytes). The dye bound to the excitable membrane yield a signal with delta F/F=12%. When the blood is added later, the dye redistributes between the "active" pool and the "passive" pool leading to decrease in total fluorescence, OP, and delta F/F. The system reaches an equilibrium at delta F/F ~5%. Additional experiments will be needed to substantiate these ideas. Additional experiments will be needed to provide more details on the dye loading mechanism in blood-perfused tissue.

JPW 6003 and 6033 exhibit an excitation wavelength (~650 nm) which was separated from the absorption maximum of blood (~580 nm). This allows use of significantly reduced excitation power, which in our experiments corresponded to an illumination level of <1 $mW/mm^2$ for an adequate fluorescent signal.

There is intense interest to extend these investigations to spiral and scroll waves in millimeter thick layers or across whole ventricular wall (thickness up to ~10 mm), with the final goal being to reconstruct 3D scroll waves. This requires new voltage sensitive dyes that exhibit excitation/emission peaks at longer wavelengths so as to provide lower light scattering, and less background fluorescence from endogenous chromophores in cardiac tissue. An additional issue is to shift the dye excitation spectrum away from the blood absorption peak. Recently the first longer-wavelength (near infrared) voltage-sensitive dyes were synthesized and have proven useful in recording cardiac and neuronal electrical activity. New optical methods, such as transillumination, narrow illuminating beam scanning, as well as transmitted light recording in combination with JPW 6003 and 6033 dyes promise to improve deeper layer imaging. Thus, in real biomedical applications, the new JPW 6003 and 6033 show many advantages over the existing blue-red repertoire of voltage sensitive dyes, such as greater depth of imaging, compatibility with blood perfused samples, and prolonged retention. Differences among the JPW 6003 and 6033 dyes in terms of lipid solubility, tissue penetrability, and ionic charge provides the opportunity to customize dyes for specific types of experimental demands. Additionally, optical mapping techniques for blood-perfused cardiac tissues is important because it is more physiological and because it is a step towards mapping in the live animal (or human, in remote future). Blood perfusion allows studying many specific features such as a stable VF baseline.

The dye JPW6003 showed delta F/F of approximately 20% in a model membrane, and in thick cardiac tissue specimens in transillumination mode (~10 mm, using excitation at 610-650 nm, emission>720 nm); and 18.7% in pig tissue. In blood perfused cardiac tissue, delta F/F was 12% for JPW6003. The other dye, JPW6033, also performed very efficiently in terms of loading, voltage sensitive signal, washout, and resistance to internalization, but does not require a vehicle such as Pluronic F-127.

TABLE 1

Fluorescence efficacies and signal to noise ratio of the styryl dyes JPW6003 and JPW6033 in different cardiac tissues

| Animal | ΔF/F (6003) | S/N (6003) | ΔF/F (6033) | S/N (6003) |
|---|---|---|---|---|
| Mouse | 9.1 ± 1.4 | 490 ± 50 | 10 ± 1.5 | 530 ± 55 |
| Rat | 11.1 ± 1.6 | 670 ± 70 | 14 ± 1.5 | 760 ± 80 |
| Guinea pig | 11.3 ± 1.0 | 715 ± 80 | 12.5 ± 1.4 | 960 ± 95 |
| Pig | 18.7 ± 1.1 | 1000 ± 100 | 15 ± 1.0 | 850 ± 90 |
| Pig* | 20 ± 1.3 | 24 ± 2.2 | 14 ± 1.1 | — |
| Pig+ | 12 ± 1.5 | — | — | — |
| Pig++ | 5.5 ± 1.5 | — | — | — |

Values are mean ± SD. Relative fluorescence ΔF/F is expressed in percent.
*transillumination
+blood perfusion, Tyrode's-perfused loading
++blood perfusion, blood-perfused loading Table 1 summarizes the maximal fluorescence efficacies, and maximal OP signal to noise ratio (S/N) for the new styryl dyes in different cardiac tissues. Efficacy of the new dyes (expressed as relative fluorescence ΔF/F), is significantly higher in JPW 6033 and JPW 6033 than di-4-ANEPPS: in any of the tested species exhibited a 50-100% higher OP amplitude. The quantum efficiency of the new dyes has not been measured, but based on other similar styryl dyes we assume it to be of the order of 0.3. Regarding tissue specific efficacy, the tendency for it to increase as the heart gets bigger, and ventricular wall also gets thicker, i.e. progressively from mouse to pig was observed. The new styryl dyes also provide better S/N ratio. This is usually important for the optical mapping of cells or cell cultures. Additionally, in transillumination mode in pig the new dyes provided much higher S/N ratio than di-4-ANEPPS. The both new dyes provide practically identical performance, the JPW6033 being a butylsulfate analog of JPW6003 (created for the purpose of better loading).

TABLE 2

The washout times of the JPW6003 and JPW6033 dyes in various species

| | Dye | |
|---|---|---|
| Animal | JPW6003 | JPW6033 |
| Mouse | 1.4 ± 0.2 | 1.0 ± 0.1 |
| Rat | 2.50 ± 0.28 | 1.8 ± 0.2 |
| Guinea pig | 2.80 ± 0.31 | 2.0 ± 0.2 |
| Pig | 3.33 ± 0.31 | 2.50 ± 0.28 |

Values are means ± SD (in hours).

Loading agent: Specifically, many of the dyes require either a loading agent, that may be toxic and/or change electrophysiological processes in the cardiac tissue; or requires loading protocols that may be not physiological, as at pH reduced to 6.0. JPW6003 to be effectively loaded with usage of pluronic F-127; switching to pluronic L64 as suggested elsewhere did not significantly improved the loading, but instead increased toxic effects. No loading agent was needed with JPW6033 (Di-4-ANBDQBS).

Raw optical action potentials (OP) are quite noisy, and for further analysis have been processed as described earlier. Negative polarity of raw action potentials observed at optimal performance of the new dyes reflects fluorescence collection on the red (longer wavelength) wing of the dye emission spectrum. Processed signals were used for all further measurement results.

All OPs are normalized in terms of delta F/F. Panel A shows OPs in Tyrode-perfused tissues, and panel B in blood-perfused tissue. The JPW 6033 and JPW 6003 dyes provided much higher OP amplitude (up to 3 times in terms of delta F/F) compared to that of di-4-ANEPPS. JPW6033 also showed a much higher OP amplitude than di-4-ANEPPS, and even in most species higher than JPW6003, except pig (for details see Table 1). However it should be noted that a somewhat higher dye concentration (several times compared to di-4-ANEPPS) has to be applied for the new styryl dyes to work effectively. The dye concentration of 10-100 µM (di-4-ANEPPS was applied at 10 µM) for bolus injection were found to stain tissue effectively, and not to produce any significant toxic effect. Longer upstroke in the OP recorded by the new dyes is related to deeper sampling of the cardiac tissue due to deeper penetration of red excitation light. There was a tendency for the OP amplitude to increase as the heart gets bigger, and ventricular wall also gets thicker. In transillumination mode, where much deeper layers contribute to the OP signal, the JPW 6033 and JPW 6003 dyes most significantly outperformed di-4-ANEPPS.

Table 1 (shown above) summarizes the maximal fluorescence efficacies (expressed as relative fluorescence ΔF/F), and maximal OP signal to noise ratio (S/N) for the JPW 6033 and JPW 6003 dyes in different cardiac tissues. Efficacy of the new dyes, is significantly higher than di-4-ANEPPS: in any of the tested species exhibited a 50-100% higher OP amplitude. The quantum efficiency of the new dyes is estimated to be of the order of 0.3. Regarding tissue specific efficacy, there was a tendency for it to increase as the heart gets bigger, and ventricular wall also gets thicker, i.e. progressively from mouse to pig. The JPW 6033 and JPW 6003 dyes also provide better S/N ratio. This is usually important for the optical mapping of cells or cell cultures. Additionally, in transillumination mode in pig the new dyes provided much higher S/N ratio than di-4-ANEPPS. Both JPW 6033 and JPW 6003 dyes provide practically identical performance, the JPW6033 being a butylsulfate analog of JPW6003.

In blood perfused pig tissue JPW6003 showed lower delta F/F values but surprisingly much better than that of di-4-ANEPPS, and comparable to di-4-ANEPPS performance in Tyrode's perfused hearts. For practical applications one should take into account that dye performance is transient and also depend on the loading method (see discussion). JPW6003 also was superior to di-4-ANEPPS in terms of signal-to-noise ratio.

Procedures and Dynamics of Dye Loading.

Table 2 (shown above) summarizes washout times of OP amplitude, which is an important parameter. 50% washout times (in hours) are provided for mouse, rat, guinea pig and pig, respectively. The values of this parameter progressively increase from mouse to rat to guinea pig, and pig.

Methods and Results: Absorbance and emission spectra in ethanol and multi-lamellar vesicles (MLV), as well as voltage-dependent spectral changes in a model lipid bilayer have been recorded. Dye performance in cardiac tissue from four animal models (mouse, rat, guinea pig and pig) was examined. The dye JPW6003 showed delta F/F of approximately 20% in a model membrane, and in thick cardiac tissue specimens in transillumination mode (~10 mm, using excitation at 610-650 nm, emission>720 nm); and 18.7% in pig tissue. In blood perfused cardiac tissue, delta F/F was 12% for JPW6003. The other dye, JPW6033, also performed very efficiently in terms of loading, voltage sensitive signal, washout, and resistance to internalization, but does not require a vehicle such as Pluronic F-127

Experimental Section

JPW 5020, JPW 3067, JPW 5034

JPW 5020, JPW 3067, JPW 5034 dyes were found to perform efficiently in various cardiac tissues and to provide OP comparable to those of di-4-ANEPPS. The two most successful dyes, JPW3067 and JPW5034, provide 40-120% of the relative fluorescence response of di-4-ANEPPS. In thin HLB layers, the new dyes provide lower relative fluorescence (5%) than di-4-ANEPPS (9%) so that their higher efficacy in cardiac tissues is related to the probing of deeper layers. In transillumination mode (when an excitation source and an emission detector are at the opposite sides of tissue) for thick cardiac tissues (>10 mm), the relative fluorescence change of the new dyes also approached or even exceeded that of di-4-ANEPPS. Optimization of filters for these dyes yet to be performed could yield further improvement in their fluorescent efficacies.

The JPW 5020, JPW 3067, JPW 5034 dyes provide advantages in the choice of excitation methods and/or light sources. Especially when working with a large area and/or thick cardiac tissues, one needs a quite powerful light source capable of providing excitation at the levels of 100 mW/cm2. When using a halogen light source with an excitation filter, shifting the central filter wavelength from 520 to 650 nm allows a several fold reduction of supplied power to the halogen bulb. Alternatively, one can use less dye or record at higher speed and still have good OP. The possible use of inexpensive excitation sources such as red LED, red laser diodes, and helium-neon lasers (at 633 nm) also represents potential advantages. All of these sources produce high dye-excitation efficiency.

Another advantage of the JPW 5020, JPW 3067, JPW 5034 dyes is lower endogenous absorption for both excitation and emission light in cardiac tissue. Most of the endogenous fluorescence was blocked by emission filters; subtraction of the autofluorescence background corrected the true background fluorescence only about 10%. According to the optical properties of cardiac tissue, shifting the wavelength 150-200 nm to the red reduces the absorption coefficient several times. Measurements show that for 10-mm-thick cardiac tissue (bloodless), this means about a 30-fold increase of excitation light in deep layers. Also, because scattering decreases with increasing wavelength, that would allow better depth resolution of the recorded OP. Finally, the JPW 5020, JPW 3067, JPW 5034 dyes have both excitation and emission spectra that are the far from the blood absorption maximum (>580 nm). This allows the possibility of using them in blood-perfused tissues.

The dynamics of dye loading, washout, and internalization was also studied. This little-studied characteristic of the dyes may be important for long-term experiments (a half hour or longer) or large area (volume) monitoring of electrical activity in cardiac tissue. In individual cell or cell culture applications, internalization of an electrochromic dye is the primary pathway for degradation of the OP, but in Langendorff type or other constantly perfused preparations, dye washout also may play an important role. No photobleaching was observed: the dynamics of the fluorescent signal are the same under permanent or intermittent (several seconds each minute) excitation.

Although there were generally no significant differences between the loading times measured using the three parameters, the washout times generally increase in the order OP background fluorescence relative potentiometric fluorescence change (delta F/F). This would be the behavior expected if dye internalization was the main factor degrading the efficacy of the potentiometric probes over time. The values of all three parameters are lowest for the dye JPW3067 and gradually increase for JPW5034 and JPW5020. This is related to the gradually increasing molecular weight (and also size) as well as the length of the hydrocarbon chains of the dye molecules. Longer hydrocarbon chains make more hydrophobic dyes that bind to a cell membrane more tightly and internalize more slowly, according to systematic studies with the ANEP dye series. During washout, the OP amplitude decreases faster than the total fluorescence, suggesting that some dye molecules are being internalized. The relatively fast loading and washout of JPW3067 can be quite an advantage in specific applications. Considering the species-specific dynamics, the dye loading and washout progressively slows down from rat to guinea pig to pig. Although metabolic rate follows a similar trend (being highest in the rat and lowest in the pig), it remains to be determined whether metabolic rate influences the washout dynamics of these dyes.

While particular embodiments of the present invention have been described herein for purposes of illustration, many modifications and changes will become apparent to those skilled in the art. Various modifications and variations of the described apparatus, kit, method, and system of the invention will be apparent to those skilled in the art without departing from the scope and spirit of the invention. Although the invention has been described in connection with specific embodiments outlined above, it should be understood that the invention should not be unduly limited to such specific embodiments. Accordingly, the appended claims are intended to encompass all such modifications and changes as fall within the true spirit and scope of this invention.

We claim:

1. A method of optical electrophysiological probing, comprising:
    providing a fluorescing chemical probe, said fluorescing chemical probe having at least one excitation wavelength such that when an electromagnetic radiation of the excitation wavelength is administered to the fluorescing chemical probe, said probe emits electromagnetic radiation at least one emission wavelength, wherein said excitation wavelength and said emission wavelength are at least about 90 nanometers apart;
    contacting a thick portion of tissue with said fluorescing chemical probe to create a thick portion of treated tissue;
    applying a first range of wavelengths of electromagnetic radiation to said treated portion of tissue, said first range of wavelengths of electromagnetic including said excitation wavelength of said fluorescing chemical probe; and
    detecting a plurality of depth-specific emission wavelengths emitted from said thick portion of treated tissue, said plurality of depth-specific emission wavelengths incremented from a surface of said thick portion of treated tissue to an inner tissue depth from about 2.5 millimeters, said depth-specific emission wavelengths emitted from said portion of treated tissue in response to said applying, wherein the fluorescing chemical probe comprises a voltage-sensitive dye of the formula:

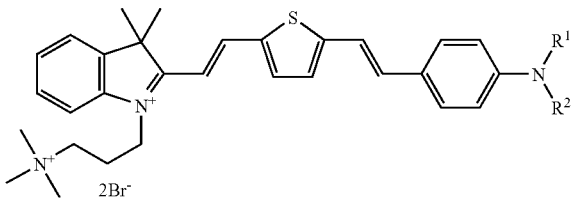

wherein R1 is a first hydrocarbon group; and
R2 is a second hydrocarbon group.

2. The method of claim 1, wherein R1 and R2 are each hydrocarbon groups having between one and about ten carbon atoms.

3. The method of claim 1, further comprising a delivery agent that is at least one of a physiologically acceptable adjuvant, solvent, substrate, or diluent.

4. The method of claim 1, wherein the delivery agent is selected from the group consisting of: Pluronic F-127, Pluronic L64, cyclodextrin, gamma cyclodextrin, dimethylsulfoxide, ethanol, and combinations thereof.

5. The method of claim 1, wherein the voltage-sensitive dye has the formula

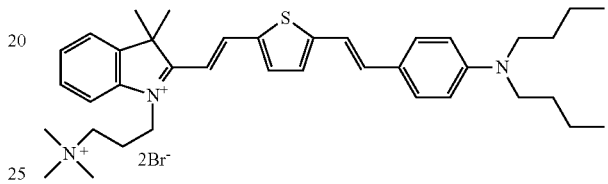

6. The method of claim 1, wherein the voltage-sensitive dye has the formula:

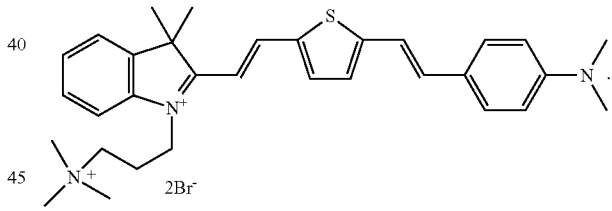

7. The method of claim 1, wherein the voltage-sensitive dye has the formula:

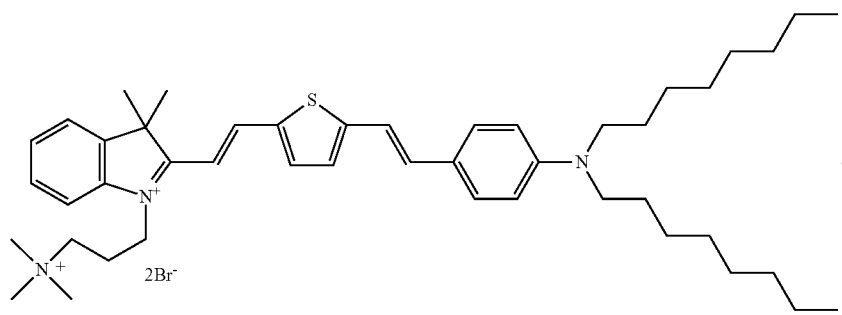

8. The composition of claim 1, wherein R1 and R2 are identical hydrocarbon groups.

9. The composition of claim 8, wherein R1 is a butyl group and R2 is a butyl group.

10. A method of optical electrophysiological probing comprising:
- providing a fluorescing chemical probe, said fluorescing chemical probe having at least one excitation wavelength such that when an electromagnetic radiation of the excitation wavelength is administered to the fluorescing chemical probe, said probe emits electromagnetic radiation at least one emission wavelength, wherein said excitation wavelength and said emission wavelength are at least about 90 nanometers apart;
- contacting a thick portion of tissue with said fluorescing chemical probe to create a thick portion of treated tissue;
- applying a first range of wavelengths of electromagnetic radiation to said treated portion of tissue, said first range of wavelengths of electromagnetic including said excitation wavelength of said fluorescing chemical probe; and
- detecting a plurality of depth-specific emission wavelengths emitted from said thick portion of treated tissue, said plurality of depth-specific emission wavelengths incremented from a surface of said thick portion of treated tissue to an inner tissue depth from about 2.5 millimeters, said depth-specific emission wavelengths emitted from said portion of treated tissue in response to said applying, wherein the fluorescing chemical probe comprises a voltage-sensitive dye having the formula:

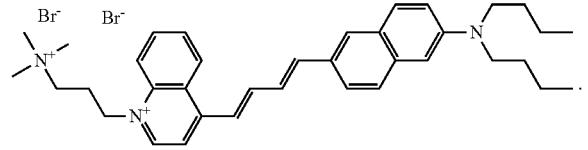

11. A method of optical electrophysiological probing, comprising:
- providing a fluorescing chemical probe, said fluorescing chemical probe having at least one excitation wavelength such that when an electromagnetic radiation of the excitation wavelength is administered to the fluorescing chemical probe, said probe emits electromagnetic radiation at least one emission wavelength, wherein said excitation wavelength and said emission wavelength are at least about 90 nanometers apart;
- contacting a thick portion of tissue with said fluorescing chemical probe to create a thick portion of treated tissue;
- applying a first range of wavelengths of electromagnetic radiation to said treated portion of tissue, said first range of wavelengths of electromagnetic including said excitation wavelength of said fluorescing chemical probe; and
- detecting a plurality of depth-specific emission wavelengths emitted from said thick portion of treated tissue, said plurality of depth-specific emission wavelengths incremented from a surface of said thick portion of treated tissue to an inner tissue depth from about 2.5 millimeters, said depth-specific emission wavelengths emitted from said portion of treated tissue in response to said applying, wherein the fluorescing chemical probe comprises a voltage-sensitive dye having the formula:

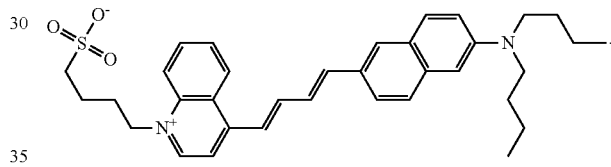

* * * * *

UNITED STATES PATENT AND TRADEMARK OFFICE
CERTIFICATE OF CORRECTION

PATENT NO.        : 8,155,730 B2
APPLICATION NO.   : 11/923282
DATED             : April 10, 2012
INVENTOR(S)       : Pertsov et al.

It is certified that error appears in the above-identified patent and that said Letters Patent is hereby corrected as shown below:

Column 1, Lines 14-18 should read:

--This invention was made with Government support under
grant HL7163501 awarded by the National Institutes of
Health. The Government has certain rights in the invention.--

Signed and Sealed this
Seventeenth Day of January, 2017

Michelle K. Lee
*Director of the United States Patent and Trademark Office*

UNITED STATES PATENT AND TRADEMARK OFFICE
CERTIFICATE OF CORRECTION

PATENT NO. : 8,155,730 B2
APPLICATION NO. : 11/923282
DATED : April 10, 2012
INVENTOR(S) : Arkady Pertsov et al.

Page 1 of 1

It is certified that error appears in the above-identified patent and that said Letters Patent is hereby corrected as shown below:

In the Specification

Column 1, Lines 14-18 should read:
Government Interest Statement
This invention was made with government support under grant nos. HL071635 and EB001963 awarded by the National Institutes of Health. The government has certain rights in the invention.

This certificate supersedes the Certificate of Correction issued January 17, 2017.

Signed and Sealed this
Nineteenth Day of September, 2023

Katherine Kelly Vidal
*Director of the United States Patent and Trademark Office*